(12) United States Patent
Koltermann et al.

US008524471B2

(10) Patent No.: US 8,524,471 B2
(45) Date of Patent: Sep. 3, 2013

(54) GENERATION OF CHEMICAL BUILDING BLOCKS FROM PLANT BIOMASS BY SELECTIVE DEPOLYMERIZATION

(75) Inventors: Andre Koltermann, Icking (DE); Ulrich Kettling, München (DE); Thomas Bruck, Ebenhausen (DE); Markus Rarbach, München (DE)

(73) Assignee: Sud-Chemie IP GmbH & Co. KG, Munich (DE)

( * ) Notice: Subject to any disclaimer, the term of this patent is extended or adjusted under 35 U.S.C. 154(b) by 1127 days.

(21) Appl. No.: 12/138,096

(22) Filed: Jun. 12, 2008

(65) Prior Publication Data
US 2009/0004697 A1 Jan. 1, 2009

Related U.S. Application Data

(60) Provisional application No. 60/943,337, filed on Jun. 12, 2007.

(30) Foreign Application Priority Data

Mar. 19, 2007 (DE) .......................... 10 2007 013 047
Jun. 12, 2007 (EP) ...................................... 07011507

(51) Int. Cl.
*C12P 19/02* (2006.01)
*C12P 21/04* (2006.01)
*C12Q 1/00* (2006.01)

(52) U.S. Cl.
USPC ............................... 435/105; 435/71.1; 435/4

(58) Field of Classification Search
USPC ............................................ 435/105, 71.1, 4
See application file for complete search history.

(56) References Cited

U.S. PATENT DOCUMENTS

| | | | |
|---|---|---|---|
| 2,444,823 A | 7/1948 | Hall et al. | |
| 4,089,745 A | 5/1978 | Antrim et al. | |
| 5,865,898 A * | 2/1999 | Holtzapple et al. | 127/37 |
| 6,090,595 A | 7/2000 | Foody et al. | |
| 6,586,212 B1 | 7/2003 | Buchanan et al. | |
| 6,692,578 B2 | 2/2004 | Schmidt et al. | |
| 6,942,754 B2 | 9/2005 | Izumi et al. | |
| 7,413,882 B2 * | 8/2008 | Berka et al. | 435/105 |
| 2003/0051836 A1 | 3/2003 | Borch et al. | |
| 2005/0136520 A1 | 6/2005 | Kinley et al. | |
| 2009/0004698 A1 * | 1/2009 | Vande Berg et al. | 435/72 |

FOREIGN PATENT DOCUMENTS

| | | |
|---|---|---|
| CN | 1840674 A | 4/2006 |
| DE | 3410455 C1 | 8/1985 |
| EP | 062 027 A2 | 3/1982 |
| EP | 0 187 422 A2 | 7/1986 |
| EP | 0 406 617 A2 | 1/1991 |
| EP | 0 884 391 A1 | 12/1998 |
| EP | 1 223 152 A | 7/2002 |
| EP | 1 548 053 A1 | 6/2005 |
| GB | 2 401 106 A | 11/2004 |
| JP | 10-248595 A | 9/1998 |
| JP | 2002-017385 A | 1/2002 |
| JP | 2002-173828 A | 6/2002 |
| JP | 2003-079388 A | 3/2003 |
| WO | WO 94/26812 A1 | 5/1994 |
| WO | WO 99/11672 A1 | 3/1999 |
| WO | WO 03/093420 A2 | 11/2003 |
| WO | WO 2005/026245 A1 | 3/2005 |
| WO | WO 2006/114095 A1 | 11/2006 |

OTHER PUBLICATIONS

Arias, M.E., et al., "Kraft Pulp Biobleaching and Mediated Oxidation of a Nonphenolic Substrate by Laccase from *Streptomyces cyaneus* CECT 3335," *Appl. Environ. Microbiol.* 69:1953-1958, American Society for Microbiology (2003).
Barr, D.P., et al., "Veratryl Alcohol-dependent Production of Molecular Oxygen by Lignin Peroxidase," *J. Biol. Chem.* 268:241-244, American Society for Biochemistry and Molecular Biology (1993).
Chen, W.P., et al., "Purification and Some Properties of β-1,3-Xylanase from *Aspergillus terreus* A-07," *Agric. Biol. Chem.* 50:1183-1194, Agricultural Chemical Society of Japan (1986).
Currie, H.A. and Perry, C.C., "Resolution of complex monosaccharide mixtures from plant cell wall isolates by high pH anion exchange chromatography," *J. Chromatogr.* 1128:90-96, Elsevier (Sep. 2006).
D'Acunzo, F., et al., "Oxidation of phenols by laccase and laccase-mediator systems," *Eur. J. Biochem.* 269:5330-5335, Blackwell Science Ltd. (2002).
Demirbaş, A., "Aqueous Glycerol Delignification of Wood Chips and Ground Wood," *Bioresour. Technol.* 63:179-185, Elsevier Science (1998).
Ferapontova, E.E., et al., "Bioelectrocatalytic properties of lignin peroxidase from *Phanerochaete chrysosporium* in reactions with phenols, catechols and lignin-model compounds," *Biochim. Biophys. Acta 1760*:1343-1354, Elsevier (Sep. 2006).

(Continued)

*Primary Examiner* — Karen Cochrane Carlson
*Assistant Examiner* — Natalie Moss
(74) *Attorney, Agent, or Firm* — Sterne, Kessler, Goldstein & Fox, P.L.L.C.

(57) ABSTRACT

The invention concerns a method for the enzymatic treatment of raw polymeric feedstock comprising the following steps: (a) preferably separation of soluble components from the raw polymeric feedstock, (b) treating the raw polymeric feedstock with an enzyme system in order to liberate defined soluble monomeric or oligomeric building blocks from the insoluble raw polymeric feedstock; and (c) separating the defined monomeric or oligomeric building blocks produced in step b) from the remainder of the raw polymeric feedstock. Preferably, the enzyme system used in step b) contains not more than 50%, preferably not more than 20%, more preferably not more than 10%, more preferably not more than 5%, more preferably not more than 2%, more preferably not more than 1% of other enzyme activities apart from the enzyme activity resulting in liberation of said defined monomeric or oligomeric building blocks from the raw polymeric feedstock according to step b). Further aspects of the invention concern the use of "less pure" and thus less costly enzyme systems in subsequent enzymatic treatment steps and methods for determining the optimum sequence of enzymatic treatment steps by analysis of the raw polymeric feedstock used.

38 Claims, 1 Drawing Sheet

(56) References Cited

OTHER PUBLICATIONS

Igarashi, K., et al., "Cellobiose dehydrogenase enhances *Phanerochaete chrysosporium* cellobiohydrolase I activity by relieving product inhibition," *Eur. J. Biochem. 253*:101-106, Blackwell Science Ltd. (1998).
Irwin, D.C., et al., "Activity Studies of Eight Purified Cellulases: Specificity, Synergism, and Binding Domain Effects," *Biotechnol. Bioeng. 42*:1002-1013, Wiley (1993).
Itoh, H., et al., "Bioorganosolve pretreatments for simultaneous saccharification and fermentation of beech wood by ethanolysis and white rot fungi," *J. Biotechnol. 103*:273-280, Elsevier (2003).
Kamitsuji, H., et al., "Direct oxidation of polymeric substrates by multifunctional manganese peroxidase isoenzyme from *Pleurotus ostreatus* without redox mediators," *Biochem. J. 386*:387-393, Oxford University Press (2005).
Kamm, B., et al., "Chapter 1: Biorefinery Systems—An Overview," in *Biorefineries—Industrial Process and Products*, Kamm, B., et al., eds., Wiley-VCH, Weinheim, Germany, pp. 3-40 (Apr. 2006).
Kersten, P.J., "Glyoxal oxidase of *Phanerochaete chrysosporium*: Its characterization and activation by lignin peroxidase," *Proc. Natl. Acad. Sci. 87*:2936-2940, National Academy of Science (1990).
Kim, E., et al., "Factorial Optimization of a Six-Cellulase Mixture," *Biotechnol. Bioeng. 58*:494-501, Wiley (1998).
Lawford, H.G. and Rousseau, J.D., "Cellulosic Fuel Ethanol," *Appl. Biochem. Biotechnol. 106*:457-469, Humana Press Inc. (2003).
Lynd, L.R., et al., "Consolidated bioprocessing of cellulosic biomass: an update," *Curr. Opin. Biotechnol. 16*:577-583, Current Biology (2005).
Mämmelä, P., "Phenolics in selected European hardwood species by liquid chromatography-electrospray ionization mass spectrometry," *Analyst 126*:1535-1538, Royal Society of Chemistry (2001).
Michel, F., et al., "Preparation and Characterisation of Dietary Fibre from Sugar Beet Pulp," *J. Sci. Food Agric. 42*:77-85, Society of Chemical Industry (1988).
Palla, G., "$C_{18}$ Reversed-Phase Liquid Chromatographic Determination of Invert Sugar, Sucrose, and Raffinose," *Anal. Chem. 53*:1966-1967, American Chemical Society (1981).
Puls, J., et al., "Biotechnical utilization of wood carbohydrates after steaming pretreatment," *Appl. Microbiol. Biotechnol. 22*:416-423, Springer-Verlag (1985).
Ramos, L.P., et al., "Conversion of Lignocellulosics to Fuels, Chemicals and Enviromentally-Friendly Materials," *Met. Mater. Process 17*:299-318, Meshap Science Publishers (2005).
Rosgaard, L., et al., "Efficiency of New Fungal Cellulase Systems in Boosting Enzymatic Degradation of Barely Straw Lignocellulose," *Biotechnol. Prog. 22*:493-498, American Chemical Society (Feb. 2006).
Saha, B.C., "Chapter 24: Enzymes as Biocatalysts for Conversion of Lignocellulosic Biomass to Fermentable Sugars," in *Handbook of Industrial Catalysis*, Hou, C.T., ed., CRC Press, Boca Raton, FL, pp. 1-12 (2005).
Sluiter, A., et al., "Determination of Structural Carbohydrates and Lignin in Biomass: Laboratory Analytical Procedure (LAP)," *Technical Report* NREL/TP-510-42618, U.S. Department of Energy (Apr. 2008).
Smirnov, S.A., et al., "Laccases from Basidiomycetes: Physicochemical Characteristics and Substrate Specificity towards Methoxyphenolic Compounds," *Biokhimiya 66*:774-779, Maik Nauka/Interperiodica (2001).
Sørensen, H.R., et al., "Synergistic enzyme mechanisms and effects of sequential enzyme additions on degradation of water insoluble wheat arabinoxylan," *Enzyme Microb. Technol. 40*:908-918, Elsevier (Mar. 2007).
Taylor, E.J., et al., "Structural insight into the ligand specificity of a thermostable family 51 arabinofuranosidase, Araf51, from *Clostridium thermocellum*," *Biochem. J. 395*:31-37, Biochemical Society (Mar. 2006).
Ward, G., et al., "Mechanistic Features of Lignin Peroxidase-catalyzed Oxidation of Substituted Phenols and 1,2-Dimethoxyarenes," *J. Biol. Chem. 278*:39726-39734, American Society for Biochemistry and Molecular Biology (2003).
Wariishi, H. and Gold, M.H., "Lignin Peroxidase Compound III," *J. Biol. Chem. 265*:2070-2077, American Society for Biochemistry and Molecular Biology (1990).
Wood, T.M. and Bhat, K.M., "Methods for Measuring Cellulase Activities," *Meth. Enzymol. 160*:87-112, Academic Press (1988).
Yoon, K.Y., et al., "Enzymatic production of pentoses from the hemicellulose fraction of corn residues," *LWT 39*:388-392, Elsevier (May 2006).
Arabinoxylan (Rye Flour) product profile as displayed at megazyme. com, accessed Jan. 8, 2009.
International Search Report for International Application No. PCT/EP2008/002223, mailed on Jul. 18, 2008, European Patent Office, Rijswijk, Netherlands.
Database esp@cenet, unverified English language abstract for German Patent DE 3410455 C1 (Listed on accompanying PTO/SB/08a as document FP2), 1985.
Berlin, A., et al., "Inhibition of cellulase, xylanase and β-glucosidase activities by softwood lignin preparations," *J. Biotechnol. 125*:198-209, Elsevier B.V., Netherlands (2006).
Gáspár, M., et al., "Corn fiber as a raw material for hemicellulose and ethanol production," *Process Biochem. 42*:1135-1139, Elsevier, Netherlands (2007).
Nechwatal, A., et al., "A Contribution to the Investigation of Enzyme-Catalysed Hydrolysis of Poly(ethylene terephthalate) Oligomers," *Macromol. Mater. Eng. 291*: 1486-1494, Wiley-VCH Verlag GmbH & Co., Germany (2006).
Zhang, Y. and Lynd, L., "Toward an Aggregated Understanding of Enzymatic Hydrolysis of Cellulose: Noncomplexed Cellulase Systems," *Biotechnol. Bioeng. 88*:797-824, Wiley, United States (2004).
Database WPI Week 199848, Derwent Publications Ltd., London, GB; AN 1998-560745, Japanese Patent No. 10248595 A, XP002431138, Sep. 22, 1998.
Standard Search Report for European Patent Application No. DE 102007013047, completed on Apr. 26, 2007, European Patent Office, Netherlands, 2 pages.
European Search Report for European Patent Application No. EP 07 01 1507, completed Jan. 4, 2008, European Patent Office, Netherlands, 3 pages.
Communication from the Examining Division for European Patent Application No. EP 08 716 639.3, dated Mar. 1, 2010, European Patent Office, Netherlands, 4 pages.
Search Opinion for European Patent Application No. 08 716 639.3, dated Oct. 5, 2011, 6 pages.
English language abstract (Unverified) for Japanese Patent No. JP 10-248595 A, Espacenet Database, European Patent Office, 2 pages (1998).
English language abstract (Unverified) for Japanese Patent No. JP 2002-017385 A, Espacenet Database, European Patent Office, 1 page (2002).
English language abstract (Unverified) for Japanese Patent No. JP 2002-173828 A, Espacenet Database, European Patent Office, 1 page (2002).
English language abstract (Unverified) for Japanese Patent No. JP 2003-079388 A, Espacenet Database, European Patent Office, 1 page (2003).
English translation of CN 1840674 A.

\* cited by examiner

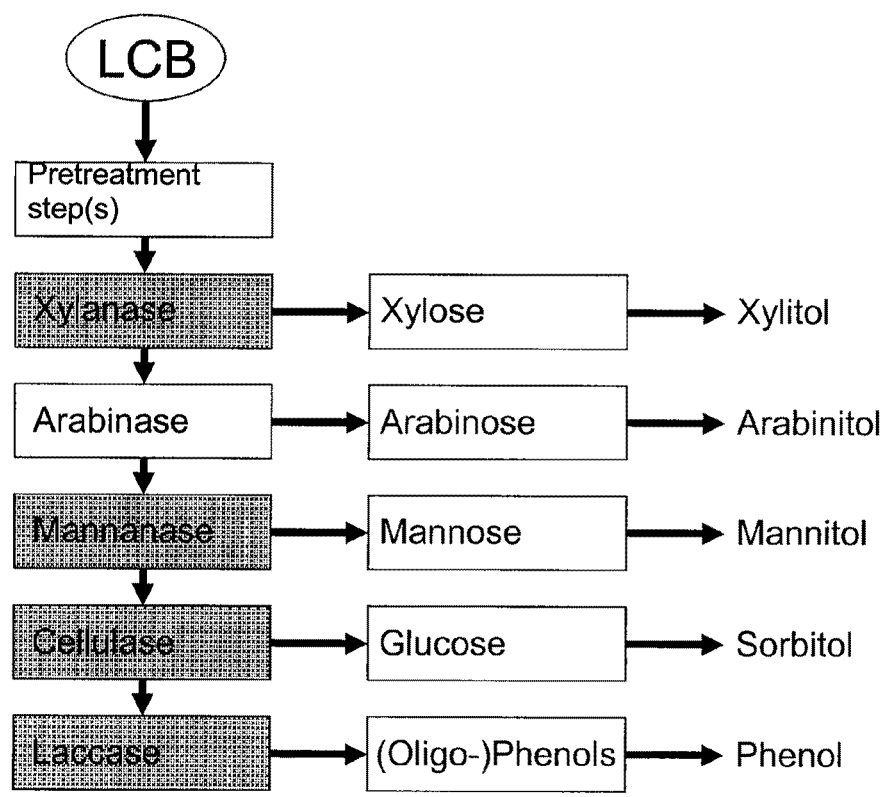

GENERATION OF CHEMICAL BUILDING BLOCKS FROM PLANT BIOMASS BY SELECTIVE DEPOLYMERIZATION

CROSS REFERENCE TO RELATED APPLICATIONS

This application claims the benefit of U.S. Provisional Patent Application No. 60/943,337, filed Jun. 12, 2008. This application also claims priority to International Patent Application No. PCT/EP2008/002223, filed Mar. 19, 2008. International Patent Application No. PCT/EP2008/002223, claims the benefit of European Patent Application No. EP 07 011 507.6, filed Jun. 12, 2007, and German Patent Application No. DE 10 2007 013 047.5, filed Mar. 19, 2007. The disclosures of each of these applications are incorporated by reference herein in their entireties.

BACKGROUND OF THE INVENTION

The generation of biobased chemical building blocks from renewable resources has recently attracted increasing attention due to the global limitation of fossil petrochemical resources. The preferred feedstocks for the generation of such biobased chemical products are derived from renewable plant biomass (Kamm et al., 2006).

The current manufacturing processes for biobased products predominantly utilize substrates from the food and feed market such as oils, sugars, and starches. Most first generation feedstocks are of well-defined chemical composition and low structural complexity. Additionally, these substrates can be obtained in relatively high purity with only minor amounts of accompanying contaminants. While their use is both technologically and economically appealing, their continuing large-scale supply is not secure because the use of first generation feedstocks in biobased chemical processes is in fierce competition with their ever increasing global demand in the food industry.

Alternative substrates of the aforementioned first generation feedstocks are derived from low cost forestry by-products and agricultural wastes constituting plant material that has no application as a food source. Examples of these designated second generation feedstocks are residual plant material from farming activities such as corn stover and wheat straw as well as various wood related wastes. This Lignocellulosic Biomass (LCB) is distinguished from first generation biological feedstocks by its complex chemical and structural composition. The primary components of LCB are highly polymeric materials such as cellulose (approx. 35-50% w/w), hemicellulose (approx. 20-35% w/w), and lignins (approx. 10-25% w/w). Proteins, lipids and other compounds constitute minor fractions in most LCB raw materials (Saha, 2005) but can be present in larger quantities in special agricultural wastes such as residues from oil production. Since LCB is composed of multiple, chemically diverse components, its downstream processing is technically difficult, which in turn limits the economic feasibility of current LCB-based bioprocesses.

Technical Problem

In order to produce valuable chemical substances and building blocks via economically viable bioprocesses based on LCB feedstocks, it is important to both (i) recover and refine the majority of its diverse chemical constituents and (ii) to produce them in sufficient purity. In contrast to the diverse and highly polymeric entities that make up LCB, its favored processing products are of low molecular weight. Principally, economically attractive products can be generated from all components of LCB: Glucose generated from cellulose is a versatile starting material for the generation of high-value chemical intermediates such as sorbitol. Pentose sugars such as xylose and arabinose deduced from hemicellulose fractions of LCB are starting materials for high-value low-nutritional and non-calorigenic sweeteners such as xylitol and arabinitol. Proteins from LCB can be hydrolyzed to yield enantiopure L-amino acids. Lignins can serve as a source of phenolic compounds substituting for aromatics produced by petrochemical processes. The current technological limitation for the use of second generation feedstocks is mainly associated with their complex chemical composition.

Most current processes that use LCBs concentrate on the cellulose part of the substrate. When other components are used they are typically hydrolyzed by unselective process steps such as pretreatment with sulphuric acid hydrolyzing all hemicelluloses in a single process step. The products of these unselective process steps are generally of low and in some cases negative commercial value.

The presently operating Iogen process for the fermentative production of bioethanol uses dilute acid steam pretreatment at 200-250° C. to mobilize the hemicellulose fraction of LCBs, which contains a mixture of different hexose and pentose sugars. In a separate enzymatic step the insoluble cellulose fraction is hydrolyzed to hexose (glucose) sugars. After liquefaction of the hemicellulose and cellulose fractions, insoluble lignin solids are physically separated from the marsh and burned to generate energy for downstream processing of the remaining LCB fractions. The combined cellulose and hemicellulose fractions are fermented together in a single step to produce bioethanol. The resulting ethanol is subsequently recovered from the fermentation broth by distillation. Since the majority of commercially available organisms (i.e. baker's yeast, *Saccharomyces cerevisiae*) used for the fermentation process are unable to utilize pentose sugars, these components of LCBs, albeit of significant commercial value when present in pure form, are discarded in the process together with remaining waste residue (Lawford and Rousseau, 2003).

Recently, attempts have been made to make the pentose fraction of LCBs available for the fermentative conversion to bioethanol. In this revised process design, the liquefied hemicellulose fraction is separated from the remaining components of LCB after the pretreatment step. While all remaining LCB fractions are processed as previously described, specially engineered microorganisms (i.e. engineered strains of *Zymomonas mobilis*) with the ability to utilize pentose (Lawford and Rousseau, 2003; Lynd et al., 2005) as well as hexose sugars are employed in a separate fermentation step to effectively convert the liquefied and conditioned hemicellulose to bioethanol. The resulting fermentation marsh is subsequently fed into the conventional process stream to recover the bioethanol. While bioethanol production from complex pentose mixtures seems to be commercially valuable, the selective processing of hexose, pentose, and lignin to high-value products and chemical building blocks is an attractive alternative route for the utilization of LCB components.

One inherent problem of all currently used pretreatment methods is the simultaneous and non-selective hydrolysis and release of various chemical building blocks that make up LCB components (Saha, 2005). At present, commercially applied and economically viable pretreatment methods employ harsh chemical or physical treatments, which may include a combination of acid or base treatments at elevated temperatures (Ramos et al., 2005). The resulting LCB hydrolysates contain a variety of unwanted by-products derived from chemical modification of LCB building blocks. The presence of these contaminants often precludes downstream enzymatic or catalytic processing or whole-cell fermentation of the products (Saha, 2005) and therefore seriously lowers the commercial value of product streams generated from LCBs by such methods.

Thus, the technical problem underlying the present invention is to provide a method for the production of chemical building blocks from renewable plant biomass.

Especially, the technical problem is to provide a method for the production of valuable chemical building blocks from LCB, which avoids the disadvantages and drawbacks of the prior art.

SUMMARY OF THE INVENTION

According to a first aspect, the present invention provides a treatment method for the enzymatic treatment of raw polymeric feedstock comprising the following steps: (a) treating the raw polymeric feedstock with an enzyme system in order to liberate defined monomeric or oligomeric building blocks from the raw polymeric feedstock and (b) separating the defined monomeric or oligomeric building blocks produced in step a) from the remainder of the raw polymeric feedstock.

According to a preferred aspect, steps a) and b) are performed in a solvent (liquid medium). Preferably, the (raw) polymeric feedstock is treated in the presence of a solvent in which it is insoluble, i.e. in which it is not present in dissolved form. Thus the (raw) polymeric feedstock preferably is an insoluble raw polymeric feedstock. The solvent is preferably an aqueous solvent. Further preferred, the enzyme step a) liberates soluble monomeric or oligomeric building blocks from the raw polymeric feedstock, i.e. monomeric or oligomeric building blocks, which are soluble in the solvent used and can thus be dissolved therein. According to a further preferred aspect, the separation of the soluble (dissolved) defined monomeric or oligomeric building blocks produced in step a) from the remainder of the insoluble (not dissolved) raw or processed polymeric feedstock (step b) is achieved by solid-liquid separation. Any conventional method for solid-liquid separation may be used, including filtration or centrifugation methods.

According to another preferred aspect, the invention comprises either a single consolidated process consisting of step a) and step b) or a series of sequential process steps, wherein step a) and step b) are repeated at least once. In each process step, soluble monomeric or oligomeric products are produced from insoluble raw or processed polymeric feedstock by successive addition of a specific enzyme system followed by the separation of the soluble monomeric or oligomeric products from the insoluble remainder of the polymeric feedstock. Any conventional method for solid-liquid separation may be used, including filtration or centrifugation methods.

According to a preferred aspect, the defined monomeric or oligomeric building block(s) liberated from the raw or processed polymeric feedstock in every treatment step a) is one specific "product" selected from the left column of Table 1 below. In other words, only one specific monomeric or polymeric building block is liberated from the raw or processed polymeric feedstock in every treatment step a) using an enzyme system or a combination of enzyme systems having the same product. Examples of such combinations of enzymes are listed in Table 1.

According to one preferred aspect of the invention it has been surprisingly found that the presence of (substantial) amounts of lignin is beneficial in the method of the invention. Thus, the selectivity and consequently the purity of the product streams obtained from the enzymatic treatment steps could be unexpectedly increased by the presence of lignin in the polymeric feedstock. The alteration in enzymatic selectivity observed may be due to altered surface properties in the presence of lignin, however, the invention is not limited to this assumption of a theoretical mechanism.

Hence, according to a preferred embodiment, the raw polymeric feedstock comprises at least 1 wt-% lignin, preferably at least 3 wt-% lignin, more preferably at least 5 wt-% lignin. Particularly advantageous results are obtained if the raw polymeric feedstock comprises at least 10 wt-% lignin, preferably at least 20 wt-% lignin. The amount of lignin present in the feedstock may be determined by methods known to the skilled person. According to one embodiment, the lignin content may be calculated in accordance with the method indicated in A. Sluiter et al., "Determination of Structural Carbohydrates and Lignin in Biomass", LAP, Technical Report NREL/TP-510-42618, January 2008. According to another embodiment, the lignin content may be calculated in accordance with the method indicated in Hsu et al., Journal of Animal Science, 1987, 65: pp. 244-255 for acid detergent lignin (ADL).

In line with the above surprising finding, according to a further preferred aspect of the invention, no ligninolytic enzyme treatment step is performed in the method of the invention. Also, it is further preferred that the content of lignin in the polymeric feedstock, calculated as wt-% of the overall composition of the polymeric feedstock, is not reduced during steps (a) and (b) or their repetition. The lignin content may be determined as outlined above.

According to a particularly advantageous aspect of the invention, the treatment method of the invention comprises at least one treatment step ("pretreatment step") prior to step a) for separating (removing) soluble components from the raw or processed (insoluble) polymeric feedstock. Thus, this step is performed prior to the enzymatic treatment of the raw or processed polymeric feedstock. It has been found that the efficiency of the subsequent enzymatic treatment step(s) can be surprisingly increased by such pretreatment step(s) for removing soluble components from the raw or processed polymeric feedstock. The preferred conditions of such pretreatment step(s) are further discussed below.

According to a preferred embodiment, the same or a similar solvent (liquid medium) as used for the following enzymatic treatment step a) is used in the pretreatment step(s). Individual pretreatment step(s) for the removal of solubles are preferably performed at the same and more preferably at higher temperatures as the following enzymatic treatment step a) to increase the extraction efficiency. Even more preferably, soluble extraction by the pretreatment step(s) will be performed at higher temperatures and pressures (pressure cooker principle) but at a shortened treatment time compared to the following enzymatic treatment step. Again, the raw or processed polymeric feedstock is preferably insoluble in the solvent used and the components to be removed are soluble therein. Separation of the soluble components from the insoluble raw or processed polymeric feedstock is preferably performed by conventional solid-liquid separation methods.

According to another embodiment of the invention, the individual pretreatment step(s) for removing soluble components from the (raw or processed) polymeric feedstock prior to step a) can be repeated in multiple stepwise cycles of at least two pretreatment steps. In a preferred embodiment, said cycles are carried out with varying solvent compositions, temperature and time profiles to increase the efficacy of soluble extraction.

The pretreatment step(s) can comprise one or more physico-chemical pretreatment step and/or one or more washing step as defined herein.

In the present invention, it has been found according to one preferred aspect that the separation of the liberated (soluble) monomeric or oligomeric building block(s) from the (insoluble) raw or processed polymeric feedstock after a defined treatment with an enzyme system provides significant advantages regarding the generation of chemically pure value-added base chemicals and chemical building blocks from complex natural substrates such as LCB by employing selective catalytic process steps. These selective catalytic process steps liberate defined chemical monomeric or oligomeric components from the complex polymeric feedstock with low amounts of other contaminants in the product generated by the process step. A preferred technical solution to provide such specificity and selectivity in the hydrolysis of LCB is the use of selective enzymatic steps. The base chemicals can be used as substituents for starting material in traditional petrochemical processes as well as starting materials for novel chemical and biochemical synthesis routes and are therefore of high commercial value.

Further preferred aspects and embodiments are described in detail below.

DETAILED DESCRIPTION OF THE DRAWINGS/FIGURES

FIG. 1 shows a process flow for the sequential enzymatic processing of LCB.

DEFINITIONS

The term "raw polymeric feedstocks" means complex mixtures of different insoluble polymeric substrates such as carbohydrates, polymeric lipids, polypeptides, polynucleotides, and polymeric phenylpropanoids in varying mass ratios that are usually derived from plant material. In addition to these insoluble polymeric substrates raw polymeric feedstocks usually contain soluble monomeric or oligomeric components. Raw polymeric feedstocks include but are not limited to waste products from the forestry, agricultural and food processing industry as well as municipal waste. When the main polymers are cellulose and lignin such raw polymeric feedstocks are termed "raw lignocellulosic feedstocks" or "lignocellulosic biomass" or "LCB". Raw lignocellulosic feedstocks from agricultural activities comprise but are not limited to wheat straw, corn stover, rumen animal manure, sugarcane bargass, sugar beet pulp, and herbaceous material like switch grass, Sericea Lespedeza Serala and *Sorghum sudan* grass. Forestry derived waste feedstocks comprise but are not limited to wood bark, wood chips, and waste timber. Lignocellulosic feedstocks derived from the food industry encompass but are not limited to fruit pulp, agave whole residue, coffee residue, and oil mill waste such as rapeseed press cake and mill effluents. Raw feedstocks derived from the pulp and paper industry include but are not limited to paper sludge and paper mill effluents. Raw feedstocks derived from municipal waste encompass but are not limited to waste paper, vegetable residue, and fruit residue.

The term "processed polymeric feedstock" as used herein shall mean the (remainder of the) raw polymeric feedstock after at least one enzymatic treatment step (step a).

The term "washing step" shall mean any pretreatment step of the raw or processed polymeric feedstock using at least one solvent in order to extract soluble components from the insoluble polymeric feedstock without modifying or changing the structure of the polymeric feedstock itself.

The term "physico-chemical treatment step" shall mean any pretreatment step of the raw or processed polymeric feedstock in order to extract soluble components from the insoluble polymeric feedstock including modifying or changing the structure of the polymeric feedstock itself.

The term "polymeric substrate" means substances composed of either a specific monomeric constituent or a limited variety of defined monomeric constituents covalently linked together in a linear or partially branched molecular structure. The insoluble fraction of raw lignocellulosic feedstocks contains significant amounts of such polymeric substrates such as cellulose, xylan, mannan, and galactan. Additionally, it also contains polymeric substrates such as lignin, arabinoxylan, glucoronoxylan, glucomannan, and xyloglucan.

The term "enzyme systems" means proteinaceous entities that are able to catalytically convert polymeric or oligomeric substrates into smaller oligomeric or monomeric constituents (building blocks). In addition to the use of a single enzyme to produce monomeric or oligomeric products from a polymeric substrate, the term enzyme system also comprises mixtures comprising more than one enzyme that produce a defined monomeric or oligomeric product by synergistic or parallel action from a polymeric feedstock. Thus, the terms "enzyme system" and "enzyme mixtures" are used interchangeably herein and both may comprise one or more enzyme or enzyme activity, respectively.

The term "monomeric or oligomeric building blocks" means monomeric or oligomeric products, which are liberated from the raw polymeric feedstock using an enzyme system. "Oligomeric" shall include compounds with two or more monomeric units.

The term "enzymatic activity" of an enzyme refers to the enzyme's catalytic activity under appropriate conditions under which the enzyme serves as a protein catalyst, which converts specific polymeric or artificial substrates to specific oligomeric or monomeric products.

The term "contaminating enzymatic activity" describes enzymatic activities of an employed enzyme system that lead to oligomeric or monomeric products other than the desired oligomeric or monomeric product(s), which are produced according to the intended (main or first) enzymatic activity of the enzyme system.

The term "artificial substrate" means a substance of commonly low molecular weight that after contacting the artificial substrate with an enzyme system gives a measurable change in the physico-chemical property of the artificial substrate that correlates to the activity of a selected enzyme system. Said physico-chemical properties and artificial substrates to give such changes in physico-chemical properties after contacting them with an enzyme system are known to those skilled in the art and comprise but are not limited to changes in spectrophotometrically measurable absorption or fluorescence emission properties, changes in chromatographic mobility to be determined by liquid or gas chromatograph and changes in molecular mass to be determined by mass spectroscopy.

Suitable artificial substrates for enzymes, enzyme systems, and measurable reaction product are listed in Table 2 below.

The term "liberate" means the conversion of an insoluble polymeric substrate to a soluble monomeric or oligomeric product by a physical, chemical, or catalytic process such as hydrolysis, oxidative or reductive depolymerization.

DETAILED DESCRIPTION OF THE INVENTION

General

The invention comprises according to a first aspect a single consolidated process or a series of sequential process steps for the generation of base chemicals or chemical building blocks from a raw polymeric feedstock. In each process step soluble monomeric or oligomeric products (building blocks) are produced from insoluble raw or processed polymeric feedstocks by contacting the raw or processed polymeric feedstock with a specific enzyme system, which is preferably essentially free of enzymatic activities producing other than the intended reaction product (monomeric or polymeric building block), followed by the separation of the soluble monomeric or oligomeric building block(s) from the insoluble raw or processed polymeric feedstock.

According to a preferred embodiment, the method comprises the separation of soluble components from (insoluble) polymeric feedstocks such as LCB prior to or in combination with the single consolidated process or prior to and in combination with one or more step(s) of a series of sequential (enzymatic) process steps as defined in the preceding paragraph.

According to another preferred embodiment of the invention, the initial separation of the soluble components from the (insoluble) raw polymeric feedstock prior to the enzymatic treatment steps comprises at least one physico-chemical pretreatment step followed by solid-liquid separation. Said physico-chemical treatment step(s) may include but are not limited to incubating the raw polymeric feedstock with a solvent under increased temperature and/or increased pressure and/or contacting the raw polymeric feedstocks with chemicals. Such chemicals include but are not limited to dilute or concentrated acids or bases. Preferably, the physico-chemical pretreatment is performed at a pH of 1-13 and more preferably a pH of either 2-5 or 8-11. According to a further preferred embodiment, the physico-chemical pretreatment is combined with one or more washing steps, preferably in order to further reduce soluble components in the raw polymeric feedstock.

According to a preferred embodiment, the pretreatment step(s) as defined herein are performed at a temperature in the range from 20 to 210° C., preferably at 50-175° C. The pressure range for each individual pretreatment step may range from 1 to 300 bar and preferentially will be in the range from 1 to 100 bar. The preferred duration of the pretreatment step(s) is dependent on the composition of the raw or processed polymeric feedstock and may range from few seconds to 1 week. Most preferentially, the treatment time for each individual pretreatment step may not exceed 1 h.

Said washing step(s) prior to the enzymatic treatment step(s) comprise at least one washing step with at least one solvent, preferably at least one aqueous solvent. Most preferred are, without limitation water or aqueous buffers. Preferably, the washing step is followed by a solid-liquid separation. According to one embodiment, the washing step is performed in the absence of an enzyme or catalyst.

In a preferred embodiment of the invention, the liquid medium used for the individual pretreatment step(s), in particular washing step(s), contains varying concentrations of inorganic salts and/or other chemical components that may affect ionic strength, pH and/or hydrophobicity of the medium to increase extractability of soluble material preferably before and after each enzymatic treatment step. Preferably, the liquid medium used for the individual pretreatment steps is characterized by a pH of 1-13. Preferably the liquid medium used for the individual pretreatment steps contains inorganic acid, bases and salts such as hydrogen chloride, sulphuric acid, ammonia, sodium chloride, sodium hydroxide, ammonium sulphate, sodium phosphate, sodium acetate, sodium citrate, sodium tartrate, sodium sulphate, and/or organic buffer components, e.g. glycine, glycerol, and/or Triton-X100 for hydrophobicity modification. Preferably, the ionic strength of the liquid medium used for the individual pretreatment steps is in the range of 0.1-10M equivalents of sodium sulphate (ionic strength I~1.7-170). In another preferred embodiment, the liquid medium is free of any organic solvent and/or compound that is not water-miscible.

In yet another preferred embodiment of the invention, individual washing step(s) are applied repeatedly to the raw or processed polymeric feedstock with varying solvent compositions using varying time, temperature and pressure profiles to maximize the extraction of a particular soluble component.

In a preferred embodiment of the invention, at least one physico-chemical pretreatment step prior to the enzymatic treatment of the raw polymeric feedstock is designed to (primarily) remove lignin, resin and/or proteinaceous components from the raw polymeric feedstock. Preferably, a liquid medium with an ionic strength (I) of more than 1 is used and, in another preferred embodiment, all subsequent pretreatment step(s), in particular washing step(s), are performed using a liquid medium with lower ionic strength than in the initial physico-chemical pretreatment step.

Methods for separation of soluble and insoluble components are known to the person skilled in the art and comprise process steps such as sedimentation, decantation, filtration, micro-filtration, ultra-filtration, centrifugation, evaporation of volatile products, and extraction with organic or inorganic solvents. According to a preferred embodiment, the pretreatment step(s) comprises a treatment with aqueous solvents, organic solvents, or any combination or mixtures of these preferably with ethanol or glycerol.

According to a preferred embodiment of the invention, the enzymatic treatment is performed in an aqueous medium, the defined monomeric or oligomeric building blocks liberated from the raw or processed polymeric feedstock are soluble in the aqueous medium, and the separation according to step b) above is performed by solid-liquid separation of the soluble building blocks in the aqueous medium from the insoluble raw or processed polymeric feedstock.

Relevant examples of polymeric substrates, which constitute major components of polymeric feedstocks, their monomeric or oligomeric degradation products (building blocks), and enzyme systems useful for generating essentially pure products from each polymeric substrate contained in a raw or processed polymeric feedstock are listed in Table 1 below.

In the processing steps of the invention, chemical building blocks of polymeric substrates like hemicellulose, cellulose, lignins, glucans, proteins, and lipids are released by contacting the polymeric feedstock with specific enzyme systems. The enzymatic decomposition of individual feedstock constituents into essentially pure soluble products is based on the application of substrate-specific enzyme preparations, which are, according to a preferred embodiment, essentially free of activities that release other constituents than the intended products in the respective process step.

Determination of Composition of Raw Polymeric Feedstock

The molecular composition of the raw feedstocks to be employed in the herein described processes can be determined by methods known to those skilled in the art. For example, the composition of lignocellulosic material may be determined using a combination of pyrolysis, gas chromatography, and mass spectrometry. A library of methods describing possible analytical methodologies for the determination of LCB components is listed under: http://www1.eere.energy.gov/biomass/analytical procedures.html#samples.

According to one embodiment, standard procedures comprising several physical and enzymatic reaction steps may be employed to empirically quantify the constituents of the polymeric feedstock on the basis of the obtained reaction products.

For common feedstocks a database listing the mass ratios for the most common feedstock classes can be found under: http://www1.eere.energy.gov/biomass/feedstock databases.html.

In an illustration to analyze the feedstock components, the raw polymeric feedstock has first to be partially hydrolyzed before further analysis can be conducted.

Prior to feedstock hydrolysis, the raw feedstock sample (1 g) should be placed into a crucible and dried at 50° C. until a constant weight is obtained. The dry weight is recorded to 3 decimal places to obtain the oven dry weight (ODW) of the sample.

For the hydrolysis procedure, 1 g of finely milled feedstock (2 μm) is placed in a pressure tube and 3 ml of 72% v/v sulphuric acid is added. The pressure tube is set in a water bath at 30° C. and incubated for 1 h. Using a stirring rod the sample has to be stirred every 5 to 10 min without removing the sample from the bath. Stirring is essential to ensure even acid to particle distribution. The acid is diluted to 4% by adding 84 ml double distilled (d.d.) water using a burette and the sample is mixed by inverting the tubes several times to eliminate phase separation.

In order to determine the acid-insoluble lignin fraction of the feedstock, the autoclaved hydrolysis solution is vacuum filtered through a previously weighed filtering crucible.

The filtrate is captured in a filtering flask and an aliquot of 50 ml is transferred into a sample storage bottle. This sample will be used in the following procedure to determine the lignin and carbohydrate content. The acid-soluble lignin determination must be performed within six hours of hydrolysis.

For the determination of acid-insoluble lignin, d.d. water is added to quantitatively transfer all remaining insolubles out of the pressure tube into the filtering crucible. The insolubles have to be rinsed with a minimum of 50 ml d.d. water and subsequently the crucible and acid-insoluble residues have to be dried at 105° C. for 4 h or until a constant weight is obtained. After incubation the samples are removed from the oven and cooled in a dessicator. The weight "w2" of the crucible and dry residue have to be recorded to the nearest 0.1 mg before the crucible and residue are placed in a muffle furnace at 575° C. for 24 h.

The crucible is carefully removed from the furnace and transferred directly into a dessicator and cooled for a specific amount of time that is equal to the initial cooling time of the crucible. The crucible and ash are weighed (weight "w3") and placed back into the furnace until a constant weight is obtained. The weight "w2" corrected for the remaining ash ("w3") is equal to the weight of acid-insoluble lignin contained in the raw feedstock.

In contrast to the complex measurements required to obtain the amount of acid-insoluble lignin, the amount of acid-soluble lignin can be easily determined spectrophotometrically. First a background measurement is run with aqueous 4% v/v sulphuric acid on a spectrophotometer of choice. Using the initial hydrolysis liquor, the absorbance at 320 nm and at the maximal absorbance of the filtrate hydrolysate, which is usually around 198 nm, is measured. The sample has to be diluted as necessary to bring the absorbance range to 0.7-1.0 A units. The absorbance of the sample to 3 decimal places is used to calculate the amount of acid-soluble lignin (ASL) present in the sample according to the calculation below:

$$\% ASL = (UV_{abs} * Volume_{filtrate} * dilution\ factor) / (e * ODW_{sample}) * 100$$

ODW=oven dry weight of raw feedstock sample $UV_{abs}$=average UV-vis absorbance for the sample at 320 nm Volume filtrate=Volume of the hydrolysis filtrate E=Extinction coefficient of biomass hydrolysate liquor at maximal absorbance of sample (numerical values of the extinction coefficients for a large number of raw polymeric feedstocks can be found in http://www1.eere.energy.gov/biomass/analytical procedures.html#samples)

The sample hydrolysate liquor may also be used to determine the structural carbohydrates contained within the hemicellulose fraction of the feedstock using an HPLC-based procedure.

This determination first requires a calibration mixture for each D-cellobiose, glucose, xylose, galactose, arabinose, and mannose. The concentrations prepared for each sugar standard should range from 0.1-4 mg/ml. For each set of calibration standards, an independent calibration verification standard (CVS) should be prepared that falls in the middle of the validated range of the calibration curve (i.e. 2.5 mg/ml). The CVS should be analyzed by HPLC after each calibration set and at regular intervals throughout the analysis sequence, bracketing groups of samples. The CVS is used to verify the quality and stability of the calibration curves of each run.

20 ml of the hydrolysis liquor obtained in the initial steps after sample hydrolysis are transferred into a 50 ml Erlenmeyer flask. Calcium carbonate is added to neutralize the sample to a pH of 5-6 and after settling of the solution the supernatant can be decanted. After settling the solution will have approximately neutral pH.

The sugar calibration standards CVS and samples are now ready for HPLC analysis using a Shodex® sugar SP0810 (Phenomenex) or an Aminex® HPX-87P (BioRad) column equipped with the appropriate guard column.

The sample injection volume should be between 10 and 50 μl dependent on concentration and detector limits. The samples are eluted with d.d. water at a flow rate of 0.6 ml/min and a column temperature of 80° C. Sample elution can be monitored best using refractive index detection.

Chromatograms should be integrated prior to analysis and individual sugar contents should be determined with reference to the appropriate standard curves for each saccharide component.

Enzyme Systems

In the embodiments described herein, the specificities of the applied enzyme mixtures are custom-tailored to obtain pure monomeric product streams (defined monomeric or polymeric building block(s)) derived from different polymeric substrate classes.

In a preferred embodiment of this invention, enzyme systems, applied to a particular raw or processed polymeric feedstock, may contain not more than 50% other enzymatic activities that may result in products other than the preferred product from a designated polymeric feedstock.

In a more preferred embodiment of this invention, enzyme system mixtures, applied to a raw or processed polymeric feedstock, may contain not more than (or less than) 20%, preferably not more than (or less than) 10%, more preferably not more than (or less than) 5%, more preferably not more than (or less than) 2%, most preferably not more than (or less than) 1% other enzymatic activities that may result in products other than the preferred product from a designated polymeric feedstock.

The percentage of other enzymatic activities may be routinely determined using standard methods for determination of the respective enzyme activity. Thus, the "main" enzyme activity present in the enzyme system leading to liberation of the desired defined monomeric or polymeric building block from the raw or processed polymeric feedstock should amount to at least 50%, preferably at least 80%, more preferably at least 90%, more preferably at least 95%, more preferably at least 98%, more preferably at least 99% of all enzyme activities present in the enzyme system.

The enzyme activities may be determined according to standard methods as known to the skilled person and as described herein.

According to one preferred embodiment, the above percentages may be simply determined by treating the raw polymeric feedstock with the enzyme system according to step a) above and analyzing the liberated soluble monomeric or oligomeric building blocks after solid-liquid separation from the insoluble raw polymeric feedstock according to step b). Thus, if the liberated monomeric or oligomeric building blocks comprise more than 50 mol-% of the specific desired building block (based on the total solids content), the other enzyme activities present in the enzyme system are considered to be less than 50%. Similarly, if the liberated monomeric or oligomeric building blocks comprise more than 80, 90, 95, 98, or 99 mol-% of the specific desired building block, the other enzyme activities present in the enzyme system are considered to be less than 20, 10, 5, 2, or 1 mol-%, respectively. Correspondingly, the "main" enzyme activity present in the enzyme system and leading to liberation of the desired defined monomeric or oligomeric building block from the raw polymeric feedstock is in this case considered to amount to at least 50%, preferably at least 80%, more preferably at least 90%, more preferably at least 95%, more preferably at least 98%, more preferably at least 99%, of all enzyme activities present in the enzyme system. According to a further embodiment, the "mol-%" is replaced by "wt-%" in the aforementioned determination of the percentage of enzyme activity (activities).

According to one embodiment, enzyme activities can be determined by measuring the rate of conversion of a chosen polymeric substrate as defined above. In an alternative embodiment the enzyme activities present in the enzyme system can be determined by using artificial substrates. Depending on the ease and reliability of the detection methods applied one can either measure the conversion of a substrate itself or alternatively the formation of a specific product resulting from the enzymatically catalyzed reaction. In special cases, catalytic intermediates of the enzyme itself (i.e. oxidoreductases) can be detected spectrophotometrically.

The testing of formulated enzyme mixtures for enzymatic activities is known to those skilled in the art. A library of suitable tests for specific enzyme activities are listed under: http://www.sigmaaldrich.com/Area_of_Interest/Biochemicals/Enzyme_Explorer/Key_Resources/Assay_Library/Assays_by_Enzyme_Name.html Examples of specific tests for determining the enzyme activities of particular enzyme classes are listed below.

In a particular case, both endo- and exo-cellulose activity can be measured in 0.5 ml of a 50 mM MES (pH 6) reaction buffer containing 10 mM $CaCl_2$, 4 mM p-nitrophenyl-beta-D-cellobioside and 200 µl of a dilute enzyme solution. The reaction should then be incubated at 50° C. for 30 min. Glycine buffer (100 mM, pH 4) is added to stop the reaction. The enzymatic activity could then be determined by measuring the amount of liberated p-nitrophenol spectrophotometrically at 430 nm. The absorbance values of p-nitrophenol are translated to micromoles of nitrophenol using a standard graph relating micromoles of nitrophenol to absorbance. One unit of cellulase activity is the amount of the enzyme required to release 1 µmol of p-nitrophenol/min under the conditions of the assay (Wood, T. M. and Bhat, K., 1988).

In another particular case, arabinofuranosidase activity can be determined in 1 ml of 50 mM sodium phosphate (pH 7) containing 4-100 µM 4-nitrophenyl-alpha-L-arabinofuranoside (pNP-Araf) and dilute enzyme solution (4 nM-8 µM). The reaction can be incubated at 37° C. and the amount of liberated 4-nitrophenol measured at 400 nm. Enzyme activity can be calculated using the extinction coefficient 10500$M^{-1}$ $cm^{-1}$ of 4-nitrophenol at 400 nm (Taylor et al., 2006).

In another particular case, xylosidase activity can be determined using an o-nitrophenol substituted-beta-D-xylopyranoside (ONP-beta-D-xylopyranoside) as a substrate (Chen et al., 1986). The substrate stock solution (10 mM) is prepared in 100 mM citrate buffer (pH 5). The dilute enzyme solution to be tested is prepared in d.d. water. The reaction containing equal molar amounts of substrate and enzyme solution in a 200 mM borate buffer at 25° C. and pH 9.8. To determine the enzyme activity, the liberation of the o-nitrophenol is recorded spectrophotometrically at a wavelength of 410 nm. The enzyme activity in units/mg of enzyme is proportional to the liberated amount of o-nitrophenol and can be calculated as described for the activity of cellulase.

In another particular case, laccase activity is determined using the guiacol oxidation assay. A stock solution of 10 mM guiacol is freshly prepared in 50 mM citrate buffer (pH 4.3, 40° C.). The reaction is carried out in 2 ml of 50 mM citrate buffer using 10 µl of dilute enzyme stock (1-3 nM) and varying amounts of substrate (5-20 µl). The rate of guiacol oxidation is then measured spectrophotometrically at 465 nm. The rate of guiacol oxidation can be determined using the extinction coefficient of 5200 $M^{-1}$ $cm^{-1}$ for guiacol oxidation products (Smirnov et al. 2001).

In another particular case, manganese peroxidase (MnP) activity can be measured in 50 mM tartrate buffer (pH 3, 25° C.) by addition of 100 µM $H_2O_2$ to a reaction mixture containing 0.5 µM/ml MnP and 5-200 µM $Mn^{2+}$. The formation of $Mn^{3+}$ is monitored spectrophotometrically at 238 nm (Kmaitisuji et al., 2005).

To determine weather a particular enzyme system (as listed in Table 1) useful for producing a desired product contains unwanted activities from any other enzyme system (as listed in Table 1) producing a different unwanted product from the same or a different polymeric substrate, one can test for this activity using a specific polymeric substrate or artificial substrate as described above by using any of the methods as described above.

For example if it is suspected that a particular enzyme system containing cellulases as listed in Table 1 contains unwanted xylosidase activity (as listed in Table 1), the primary cellulase activity can be tested first using an artificial cellulose substrate and determine the amount of glucose liberated after addition of a defined amount of the enzyme system in a unit time. Once the cellulase activity of the preparation has been determined, the same enzyme preparation can be tested for xylosidase activity by contacting the enzyme system with an artificial xylan substrate and subsequently measuring the amount of xylose liberated by a defined amount of enzyme in unit time. By measuring the relative conversion rates for a defined time period with both the cellulase and xylosidase substrates using a defined enzyme amount, the specific activities for each substrate class can be calculated.

Useful substrates for determination of any enzymatic activity as listed in Table 1 are listed in Table 2.

In an alternative embodiment an approach to determine if an enzyme system contains any independent contaminating enzyme activity is to separate the components of said preparation by methods such as electrophoresis or chromatography. The individual components of the preparation can be detected using specific methods such as calorimetric staining or detection of constituents by absorbance or other methods known to those skilled in the art. The relative % distribution of proteinaceous constituents can be determined using quantitative methods such as densitometry or any other equivalent method known to those skilled in the art in conjunction with appropriate mathematical calculations.

Determination of Sequence

Prior to individual or serial enzymatic treatment steps required to liberate defined monomeric or oligomeric products (building blocks) from a raw or processed polymeric feedstock, soluble components of the raw polymeric feedstock are preferably separated by one or a number of pretreatment step(s).

In a preferred embodiment of the invention, the pretreatment step(s) to separate the soluble components of the raw or processed polymeric feedstock prior to enzymatic treatment is a combination of at least one physico-chemical pretreatment step and one or more washing step. According to another preferred embodiment of the invention, the washing step(s) to separate the soluble components from the raw or processed polymeric feedstock prior to enzymatic treatment is (are) preferentially performed with hydrophilic solvent(s), preferably aqueous solvent(s) such as water. As stated above, it has been found that the washing step(s) and physico-chemical pretreatment step(s) enhance the efficiency of the subsequent enzymatic treatment step(s).

According to a further preferred embodiment, a physico-chemical pretreatment step is only employed prior to the first enzymatic treatment step (step a) of the raw polymeric feedstock. Such physico-chemical pretreatment step may be combined with at least one washing step prior to the first enzymatic treatment step (step a) of the raw polymeric feedstock. Further preferred, pretreatment steps of the processed polymeric feedstock only comprise at least one washing step but no further physico-chemical pretreatment step.

Physico-chemical pretreatment steps for polymeric feedstocks may include without limitation hot water extraction, low temperature steam explosion, acid steam explosion, ammonia steam explosion, and sonication. They can be used to physically modify raw polymeric substrates in order to increase surface accessibility of plant fibers and decrease the crystallinity of the cellulose fraction (Puls et al., 1985; Ramos et al., 2005; Kinley et al., 2005). Preferentially, the above mentioned pretreatment steps alter the physical properties of raw polymeric substrate structure in a way that renders the substrate more accessible to subsequent enzymatic steps but release either limited amounts or none of its chemical building blocks. In addition, they can be used to further remove soluble substances contained in the raw polymeric feedstock, before contacting the raw polymeric feedstock with an enzyme system to prevent contamination of the products of this enzymatic process step by soluble substances contained in the feedstock.

When two or more process steps are employed sequentially, the sequence of these process steps and thereby the sequence of adding enzyme mixtures as described in Table 1 depends on the specific composition of raw polymeric feedstock used. The sequence of process steps and enzyme systems is chosen in a way that minimizes dosage and costs of enzyme catalysts as well as the feedstock contact time leading to the release of the desired products. Additionally, chosen sequence steps should optimize purity as well as profitability of the monomeric or oligomeric reaction products released from the polymeric substrate. The sequence of process steps is therefore feedstock and product dependent.

According to one preferred embodiment of the invention, the enzyme or enzyme system used in the first enzymatic treatment step a) is selected from the group of glucose-liberating enzymes or enzyme systems according to Table 1, and the defined soluble monomeric or oligomeric building block is glucose, and the enzyme or enzyme system used in the second enzymatic treatment step a) is selected from the group of xylose-liberating enzymes or enzyme systems according to Table 1, and the respective defined soluble monomeric or oligomeric building block is xylose.

According to another preferred embodiment of the invention, the enzyme or enzyme system used in the first enzymatic treatment step a) is selected from the group of xylose-liberating enzymes or enzyme systems according to Table 1, and the defined soluble monomeric or oligomeric building block is xylose, and the enzyme or enzyme system used in the second enzymatic treatment step a) is selected from the group of glucose-liberating enzymes or enzyme systems according to Table 1, and the respective defined soluble monomeric or oligomeric building block is glucose.

According to one preferred embodiment, the specific sequence of enzyme treatments necessary for the decomposition of a particular feedstock into its unit constituents can be determined empirically, even if the feedstock composition is unknown. Therefore, it is possible to digest the raw polymeric feedstock in separate treatment steps with a number of enzyme mixtures of different products as listed in Table 1. For each of the treatment steps the purity and composition of the resulting product stream is measured by using analytical methods known to the person skilled in the art comprising but not limited to spectroscopic and chromatographic methods as described previously for the analysis of the feedstock composition and for determining the enzymatic activity.

Using the results of these measurements, it is then possible to select the kinetically favorable enzyme mixture resulting in the purest product streams as the primary feedstock treatment step. After repeated washing of the insoluble remains resulting from this particular enzyme treatment, the remains are processed again with another number of enzyme mixtures, except with the enzyme mixture selected for the primary treatment. For all of these enzyme treatments the resulting product composition is determined by methods as described previously. The enzyme mixture resulting in the purest product stream is selected as the secondary treatment step of a particular feedstock. The remaining insoluble material derived from the second processing is again thoroughly washed and again tested with all remaining enzyme systems as described above. This process of analytically determining and selecting the purest product streams resulting from each of the remaining enzyme mixtures in Table 1 is preferably repeated until the feedstock is either decomposed completely or the insoluble feedstock residues remaining after repeated enzyme treatments do not pose a major economical gain to the operator in comparison to the cost of further treatment options.

According to one preferred aspect of the invention, the enzyme system giving the highest purity of the defined soluble monomeric or oligomeric building blocks after treatment of the raw polymeric feedstock with the enzyme system and separation of the defined soluble monomeric or oligomeric building blocks from the remainder of the raw polymeric feedstock (processed polymeric feedstock) is chosen for the first enzymatic treatment step according to step a).

According to a further preferred aspect of the invention, the second enzyme system chosen for the second enzymatic treatment step according to step a) is the one which gives the highest purity of the defined soluble monomeric or oligomeric building blocks after treatment of the processed polymeric feedstock (obtained as remainder from the previous enzymatic treatment step) with the enzyme system and separation of the defined soluble monomeric or oligomeric building blocks from the raw polymeric feedstock.

According to yet a further preferred aspect of the invention, any subsequent enzyme treatment steps are performed in the order of decreasing purity of the defined soluble monomeric or oligomeric building blocks obtained after treatment of the processed polymeric feedstock (obtained from the previous enzyme treatment step) with the respective enzyme system and separation of the defined soluble monomeric or oligomeric building blocks from the processed polymeric feedstock.

In another option the feedstock composition is determined by aforementioned analytical procedures prior to sequence selection for enzymatic treatment options. Thus, according to a preferred embodiment of the invention, the enzyme systems to be employed and their sequence of use are determined by first analyzing the raw polymeric feedstock.

One such preferred embodiment of the invention is directed to a method, in particular to determine the enzyme systems to be used and their sequence, wherein, preferably after separating soluble components from the raw polymeric substrate as described above, the insoluble raw polymeric feedstock is (a) first treated in separate enzymatic treatments with each of a plurality of enzyme systems (mixtures) such as listed in Table 1 (preferably selected from those liberating soluble monomeric or oligomeric saccharide building blocks from the polymeric feedstock);

(b) For each enzymatic treatment, the defined monomeric or oligomeric building blocks liberated from the raw polymeric feedstock are analyzed for purity of the defined monomeric or oligomeric building blocks, preferably after solid-liquid separation of the (soluble) defined monomeric or oligomeric building blocks from the (insoluble) raw polymeric feedstock;

(c) The enzyme system giving the highest purity is chosen for the first enzymatic treatment step according to step a) of claim 1;

(d) Optionally, the sequence of steps a) to c) is repeated with the remainder of the raw or processed polymeric feedstock in order to determine the enzyme system to be used in the subsequent enzymatic treatment step.

In an alternative embodiment, after separating soluble components from the raw or processed polymeric feedstock as described above, selective enzyme mixtures as listed in Table 1 are applied to target the feedstock constituent contributing the largest mass ratio to the feedstock composition. After enzymatic treatment, the purity of the resulting product stream has to be determined as previously described for the analytical determination of the feedstock components. It is desired, according to a preferred embodiment, that the purity is such that more than 75 wt-%, preferably more than 90 wt-%, more preferably more than 95 wt-%, more preferably more than 99 wt-% of the total solids content (preferably of the soluble fraction) consists of the defined monomeric or oligomeric building blocks.

If enzymatic decomposition of the largest mass feedstock component results in a pure product stream (as defined above), this treatment can be applied as the primary step for the feedstock processing. Washing of the resulting insoluble mash and subsequent solid-liquid separation of the particulate from the supernatant will prepare for the next processing steps. The remaining insolubles derived from the primary feedstock treatment will be treated with specific enzyme systems, such as the enzyme systems listed in Table 1, that target the feedstock constituents constituting the second largest mass ratio to the feedstock composition. The resulting product stream again has to be analyzed by said analytical methods to ascertain product purity before the selected enzymatic treatment can be deemed as the second treatment option for feedstock processing. The resulting insoluble residues of the secondary enzymatic treatment can then be washed and processed as described previously. Through iterative treatments with specific enzyme systems listed in Table 1, which always target the polymeric substrate constituting the largest mass ratio constituent in the remaining insoluble feedstock residue resulting from previous enzymatic treatment cycles, the feedstock can sequentially be decomposed into its unit constituents.

A further preferred aspect of the invention is directed to a method, in particular to determine the enzyme systems to be used and their sequence, wherein, preferably after separating soluble components from the raw polymeric feedstock as described above the insoluble raw polymeric feedstock is (a) first treated in separate enzymatic treatments with each of a plurality of enzyme systems (mixtures) such as listed in Table 1 (preferably selected from those liberating soluble monomeric or oligomeric saccharide building blocks from the polymeric feedstock) to determine the monomeric or oligomeric building blocks contributing the largest mass ratio in the raw polymeric feedstock;

(b) The defined monomeric or oligomeric building blocks contributing the largest mass ratio in the raw polymeric feedstock are analyzed for purity, preferably after separation from the raw polymeric feedstock;

(c) If the purity as determined is such that more than 75 wt-%, preferably more than 90 wt-%, more preferably more than 95 wt-%, more preferably more than 99 wt-% of the total solids content consists of the defined monomeric or oligomeric building blocks, the respective enzyme system is chosen for the first enzymatic treatment step according to step a) of claim 1;

(d) If the purity determined according to step b) is lower than required according to step c), the defined monomeric or oligomeric building blocks contributing the next largest mass ratio in the raw polymeric feedstock are analyzed for purity, preferably after solid-liquid separation from the (insoluble) raw polymeric feedstock accordingly, until the purity satisfies the requirement according to step c) and the respective enzyme system is chosen for the first enzymatic treatment step according to step a) of claim 1;

(e) Optionally, the sequence of steps a) to d) is repeated with the remainder of the raw or processed polymeric feedstock in order to determine the enzyme system to be used in the subsequent enzymatic treatment step.

Yet a further preferred aspect of the invention is directed to a method, in particular to determine the enzyme systems to be used and their sequence, wherein the raw polymeric feedstock is (a) first treated in separate enzymatic treatments with each of a plurality of enzyme or enzyme systems (mixtures) such as listed in Table 1 (preferably selected from those liberating soluble monomeric or oligomeric saccharide building blocks from the polymeric feedstock) to determine the enzymatic treatment that leads to the highest yield of monomeric or oligomeric building blocks contained in the raw polymeric feedstock;

(b) Those enzymatic treatments are selected that yield a defined monomeric or oligomeric product with a purity of more than 75 wt-%, preferably more than 90 wt-%, more preferably more than 95 wt-%, more preferably more than 99 wt-% of the total solids (preferably after separation from the insoluble raw or processed polymeric feedstock);

(c) Among the remaining enzymatic treatments, the treatment with the highest yield of monomeric or oligomeric product is determined;

(d) Optionally the sequence of steps a) to c) is repeated with the remainder of the raw or processed polymeric feedstock in order to determine the enzyme system to be used in the subsequent enzymatic treatment step.

According to a further preferred aspect of the invention, the enzyme systems used in the enzymatic treatment steps are employed in a sequence in accordance with the sequence obtainable according to the above methods of determining the enzyme systems to be used.

According to another preferred aspect of the invention, the enzyme systems for which a determination of the advantageous sequence of application has been discussed above comprise or consist of enzymes liberating soluble monomeric or oligomeric saccharide building blocks from the (raw) polymeric feedstock. According to a further preferred embodiment of the invention, the respective enzymes and enzyme systems are those having a (main) activity directed to the degradation of oligo or polysaccharides and/or liberating soluble monomeric or oligomeric saccharide building blocks from the raw or processed polymeric feedstock.

According to one embodiment, for the determination of the yield or purity of the defined soluble monomeric or oligomeric building blocks (product) obtained in a particular enzyme treatment following separation of the defined soluble monomeric or oligomeric building blocks from the (remaining insoluble) raw or processed polymeric feedstock after the enzyme incubation, the hydrolysis suspension (with the enzyme and the polymeric feedstock) was centrifuged at 10.000 g for 15 min. The supernatant (comprising the defined soluble monomeric or oligomeric building blocks) was processed as described hereinafter in the Examples and subjected to HPAE-PAD analysis (Dionex, Ca., USA, 6) to determine its sugar and uronic acid composition.

As stated above, according to a preferred aspect of the invention, the enzyme systems employed should be low in or essentially void of other or contaminating enzyme activities that liberate other than the intended monomeric or oligomeric building blocks from the raw or processed polymeric feedstock.

Thus according to a preferred embodiment, the enzyme system used in a particular enzymatic treatment step contains not more than 50%, preferably not more than 20%, more preferably not more than 10%, more preferably not more than 5%, more preferably not more than 2%, more preferably not more than 1% of contaminating (other) enzymatic activities, which have not been employed in a previous enzymatic treatment step using a different enzyme system or which can cause liberation of other defined monomeric or oligomeric building blocks that have not been liberated in previous enzymatic treatment steps, or, according to one further embodiment, which can only cause liberation of products from polymeric substrates that are initially essentially absent from the polymeric feedstock. The percentage of other or contaminating enzyme activities in the enzyme system may be calculated as set out above. "Essentially absent from", according to a preferred embodiment, means less than 20 wt-%, preferably less than 10 wt-%, preferably less than 5 wt-%, preferably less than 2 wt-%, preferably less than 1 wt-% of the total polymeric feedstock.

However, according to an advantageous and preferred embodiment of the invention, the enzyme system employed in a particular enzymatic treatment step contains as contaminating enzymatic activities one or more of such enzymatic activities, which have been employed in a previous enzymatic treatment step using a different enzyme system, or, according to a further embodiment, enzyme systems, which can only cause liberation of other monomeric or oligomeric building blocks from polymeric substrates that are initially essentially absent in the raw or processed polymeric feedstock. In other words, it has been found that when a particular monomeric or oligomeric building block has been previously liberated from the raw or processed polymeric feedstock in a previous enzymatic treatment step (or was not present in the raw polymeric feedstock from the beginning), it is not essential that the enzyme system used in a subsequent step is essentially free of the respective enzyme activity used as main activity in any of the previous enzymatic treatment step. One advantage of this embodiment is that less pure and thus less costly enzyme systems may be used in the second and following enzymatic treatment steps.

In a specific case of such a process the enzymatic conversion of xylan to xylose is performed in one process step after enzymatic processing of cellulose with subsequent removal of the product glucose in a previous process step. Hence, the enzyme mixtures in Table 1 designated for the processing of xylan to xylose may also contain any contaminating enzymatic activities, which are specific for the processing of cellulose.

Additionally, according to a further preferred embodiment of the invention, enzyme systems used for processing of a particular raw or processed polymeric feedstock constituent may contain contaminating (other) enzyme activities if these act on specific reaction intermediates resulting from the former enzymatic reactions and if the final end products are identical. In other words, a further preferred embodiment of the invention is directed to a method wherein the enzyme system used in a particular enzymatic treatment step has a main enzymatic activity (as described above) and contains at least one additional enzymatic activity which leads to the same defined monomeric or oligomeric building block(s) from the raw or processed polymeric feedstock as the main enzymatic activity of the enzyme system, in particular from a different polymeric substrate present in the raw or processed polymeric feedstock.

In a specific case the raw polymeric substrate contains both cellulose and starch (amylose) and the product of interest in the respective process step is glucose. Then the contamination of an enzyme mixture designated in Table 1 for the conversion of cellulose (cellulase activities) with accompanying side activities for the conversion of starch (amylase activities) as designated in Table 1 can be tolerated. The enzyme system therefore must not contain other enzyme activities above a certain ratio except for amylase activities. Here, the educts for the different enzymatic reactions may differ but the product in each case is glucose.

According to one preferred embodiment, the feedstock is a cellulose-xylan-rich feedstock and the enzyme or enzyme system used in the first enzymatic treatment step a) is selected from the group of glucose-liberating enzymes or enzyme systems according to Table 1, and the defined soluble monomeric or oligomeric building block is glucose, and the enzyme or enzyme system used in the second enzymatic treatment step a) is selected from the group of xylose-liberating enzymes or enzyme systems according to Table 1, and the defined soluble monomeric or oligomeric building block is xylose. In this embodiment it is further preferred that the enzyme or enzyme system used in the first step a) is selected from the group: Beta-glucosidase from *A. niger* or from *T. reesei*; Cellobiohydrolase II-II from *T. reesei*; Endo-beta-1-4-D-glucanase I-V from *T. reesei*, and the enzyme or enzyme system used in the second step a) is selected from the group: Endoxylanase from *A. niger* or *T. reesei* or *C. thermocellum*; Xylosidase from *A. niger* or *T. reesei*.

According to another preferred embodiment, the feedstock is a cellulose-xylan-rich feedstock and the enzyme or enzyme system used in the first enzymatic treatment step a) is selected from the group of xylose-liberating enzymes or enzyme systems according to Table 1, and the defined soluble monomeric or oligomeric building block is xylose, and the enzyme or enzyme system used in the second enzymatic treatment step a) is selected from the group of glucose-liberating enzymes or enzyme systems according to Table 1, and the defined soluble monomeric or oligomeric building block is glucose. In this embodiment it is further preferred that the enzyme or enzyme system used in the first step a) is selected from the group: Endoxylanase from *A. niger* or *T. reesei* or *C. thermocellum*; Xylosidase from *A. niger* or *T. reesei*, and the enzyme or enzyme system used in the second step a) is selected from the group: Beta-glucosidase from *A. niger* or from *T. reesei*; Cellobiohydrolase I-II from *T. reesei*; Endo-beta-1-4-D-glucanase I-V from *T. reesei*.

According to another preferred embodiment, the feedstock is an arabinan-pectin-rich feedstock and the enzyme or enzyme system used in the first enzymatic treatment step a) is selected from the group of arabinose-liberating enzymes or enzyme systems according to Table 1, and the defined soluble monomeric or oligomeric building block is arabinose, and the enzyme or enzyme system used in the second enzymatic treatment step a) is selected from the group of uronic acid-liberating enzymes or enzyme systems according to Table 1, and the defined soluble monomeric or oligomeric building block is uronic acid. In this embodiment it is further preferred that the enzyme or enzyme system used in the first step a) is selected from the group: Endoarabinase from *A. niger*; Arabinofucosidase from *A. niger*, and the enzyme or enzyme system used in the second step a) is selected from the group: Pectinase (pectate lyase, polygalactourenase) from *A. aculeatus, A. niger* or *C. japonicus*.

According to another preferred embodiment, the feedstock is an arabinan-pectin-cellulose-rich feedstock and the enzyme or enzyme system used in the first enzymatic treatment step a) is selected from the group of arabinose-liberating enzymes or enzyme systems according to Table 1, and the defined soluble monomeric or oligomeric building block is arabinose, the enzyme or enzyme system used in the second enzymatic treatment step a) is selected from the group of glucose-liberating enzymes or enzyme systems according to Table 1, and the defined soluble monomeric or oligomeric building block is glucose, and the enzyme or enzyme system used in the third enzymatic treatment step a) is selected from the group of uronic acid-liberating enzymes or enzyme systems according to Table 1, and the defined soluble monomeric or oligomeric building block is uronic acid. In this embodiment it is further preferred that the enzyme or enzyme system used in the first step a) is selected from the group: Endoarabinase from *A. niger*; Arabinofucosidase from *A. niger*, the enzyme or enzyme system used in the second step a) is selected from the group: Beta-glucosidase from *A. niger* or from *T. reesei*; Cellobiohydrolase I-II from *T. reesei*; Endo-beta-1-4-D-glucanase I-V from *T. reesei*, and the enzyme or enzyme system used in the third step a) is selected from the group: Pectinase (pectate lyase, polygalactourenase) from *A. aculeatus, A. niger* or *C. japonicus*.

According to another preferred embodiment, the feedstock is an galactan-pectin-rich feedstock and wherein the enzyme or enzyme system used in the first enzymatic treatment step a) is selected from the group of galactose-liberating enzymes or enzyme systems according to Table 1, and the defined soluble monomeric or oligomeric building block is galactose, and wherein the enzyme or enzyme system used in the second enzymatic treatment step a) is selected from the group of uronic acid-liberating enzymes or enzyme systems according to Table 1, and the defined soluble monomeric or oligomeric building block is uronic acid. In this embodiment it is further preferred that the enzyme or enzyme system used in the first step a) is selected from the group: Endogalactonase from *A. niger* or from *C. thermocellum*; beta-Galactosidase from *A. niger* or *K. fragilis*, and the enzyme or enzyme system used in the second step a) is selected from the group: Pectinase (pectate lyase, polygalactourenase) from *A. aculeatus, A. niger* or *C. japonicus*.

According to another preferred embodiment, the feedstock is a mannan-xylan-rich feedstock and the enzyme or enzyme system used in the first enzymatic treatment step a) is selected from the group of mannose-liberating enzymes or enzyme systems according to Table 1, and the defined soluble monomeric or oligomeric building block is mannose, and the enzyme or enzyme system used in the second enzymatic treatment step a) is selected from the group of xylose-liberating enzymes or enzyme systems according to Table 1, and the defined soluble monomeric or oligomeric building block is xylose. In this embodiment it is further preferred that the enzyme or enzyme system used in the first step a) is selected from the group: Endo-Mannanase from *A. niger, B. subtilis, T. maritima* or from *T. reesei*; Exo-Mannosidase from *C. fimi*, and the enzyme or enzyme system used in the second step a) is selected from the group: Endoxylanase from *A. niger* or *T. reesei* or *C. thermocellum*; Xylosidase from *A. niger* or *T. reesei*.

According to another preferred embodiment, the feedstock is a mannan-cellulose-rich feedstock and the enzyme or enzyme system used in the first enzymatic treatment step a) is selected from the group of mannose-liberating enzymes or enzyme systems according to Table 1, and the defined soluble monomeric or oligomeric building block is mannose, and the enzyme or enzyme system used in the second enzymatic treatment step a) is selected from the group of glucose-liberating enzymes or enzyme systems according to Table 1, and the defined soluble monomeric or oligomeric building block is glucose. In this embodiment it is further preferred that the enzyme or enzyme system used in the first step a) is selected from the group: Endo-Mannanase from *A. niger, B. subtilis, T. maritima* or from *T. reesei*; Exo-Mannosidase from *C. fimi*, and the enzyme or enzyme system used in the second step a) is selected from the group: Beta-glucosidase from *A. niger* or from *T. reesei*; Cellobiohydrolase I-II from *T. reesei*; Endo-beta-1-4-D-glucanase I-V from *T. reesei*.

The following are further preferred embodiments of the invention, indicating a sequence of enzymatic treatment steps depending on the nature or composition of the raw polymeric feedstock used.

1. For Xylan/Cellulose rich feedstocks (e.g. straw), i.e. feedstocks with >10 wt-% Xylan, >10 wt-% Cellulose and <15 wt-% Arabinan, the following sequence of enzymatic treatment steps is preferably employed:
   1.) Xylan depolymerisation/degradation
   2.) Cellulose depolymerisation/degradation
2. For Arabinan/Pectin rich feedstock (e.g. Beet), i.e. feedstocks with >15 wt-% Arabinan, >10 wt-% Pectin, <10 wt-% Cellulose and <10 wt-% Xylan the following sequence of enzymatic treatment steps is preferably employed:
   1.) Arabinan depolymerisation/degradation
   2.) Pectin depolymerisation/degradation
3. For Arabinan/Pectin/Cellulose rich feedstocks, i.e. feedstocks with >15 wt-% Arabinan, >10 wt-% Pectin, >10 wt-% Cellulose and <10 wt-% Xylan the following sequence of enzymatic treatment steps is preferably employed:
   1.) Arabinan depolymerisation/degradation
   2.) Cellulose depolymerisation/degradation
   3.) Pectin depolymerisation/degradation
4. For Arabinan/Xylan/Pectin/Cellulose rich feedstocks, i.e. feedstocks with >15 wt-% Arabinan, >10 wt-% Xylan, >10 wt-% Pectin and >10 wt-% Cellulose the following sequence of enzymatic treatment steps is preferably employed:
   1.) Arabinan depolymerisation/degradation
   2.) Xylan depolymerisation/degradation
   3.) Cellulose depolymerisation/degradation
   4.) Pectin depolymerisation/degradation
5. For Galactan/Pectin rich feedstocks (i.e. Potato Pectic Galactan), i.e. feedstocks with >10 wt-% Galactan, >10 wt-% Pectin, <15 wt-% Arabinan and <10 wt-% Xylan the following sequence of enzymatic treatment steps is preferably employed:
   1.) Galactan depolymerisation/degradation
   2.) Pectin depolymerisation/degradation
6. For mannan/xylan rich feedstocks, i.e. feedstocks with >15 wt-% Mannan, >10 wt-% Xylan, <15 wt-% Arabinan and <10% Cellulose the following sequence of enzymatic treatment steps is preferably employed:
   1.) Xylan depolymerisation/degradation
   2.) Mannan depolymerisation/degradation
7. For mannan/xylan/arabinan rich feedstock (e.g. coffee been hulls), i.e. feedstocks with >15 wt-% Mannan, >10 wt-% Xylan, >15 wt-% Arabinan and <10 wt-% Cellulose the following sequence of enzymatic treatment steps is preferably employed:
   1.) Arabinan
   2.) Xylan depolymerisation/degradation
   3.) Mannan depolymerisation/degradation
8. For Galactan rich feedstock (e.g. Larchwood Arabinogalactan; Guar Galactomannan), i.e. feedstocks with >10 wt-% Galactan, <10 wt-% Pectin and <10 wt-% Xylan the following sequence of enzymatic treatment steps is preferably employed:
   1.) Galactan depolymerisation/degradation
   2.) Xylan or Arabinan depending on composition of feedstock.
   3.) Mannan depolymerisation/degradation
9. For Mannan/Cellulose rich feedstocks (e.g. Konjak Glucomannan), i.e. feedstocks with >15 wt-% Mannan, >10 wt-% Cellulose, <10 wt-% Xylan, <10 wt-% Galactan and <15 wt-% Arabinan the following sequence of enzymatic treatment steps is preferably employed:
   1.) Mannan depolymerisation/degradation
   2.) Cellulose depolymerisation/degradation In the preferred case the said enzyme mixtures applied have to be essentially free of specific enzymatic activities that would result in the contamination of the resulting product stream.

In another specific case where glucose is a product of interest and the raw polymeric feedstock contains cellulose as a polymeric substrates (e.g. wheat straw), an enzyme mixture of cellulases is applied. Useful enzyme mixtures are designated in Table 1. Such cellulase mixtures can be used in conjunction with beta-glycosidases, glucohydrolases, and alpha- or beta-amylases as listed in Table 1 to convert the cellulose fraction of the raw polymeric feedstock to monomeric glucose units. In order to obtain a pure product stream of glucose, the enzyme mixture applied to the cellulose fraction has to be free of any hemicellulase activities, which encompass but are not limited to enzyme activities of arabinofuranosidase, arabinase, galactosidase, mannanase, mannanosidase, xylanase, and xylosidase. In this enzymatic process the polymeric cellulose will be transformed to soluble glucose units, which can be physically separated from the insoluble feedstock as described above. The remaining insoluble material can be processed further to produce various pentose sugars from the hemicellulose fraction.

In another specific case where arabinose and xylose are products of interest and the raw polymeric feedstock contains polymeric substrates comprising heterogeneous hemicellulose polymers such as arabinoxylan, an enzyme mixture designated in Table 1 for the conversion and mobilization of branched arabinose units is applied first. Subsequently, the soluble arabinose units are separated from the remaining insoluble feedstock before a second enzyme mixture designated in Table 1 is applied to mobilize the xylose units contained in xylan polymers. The soluble xylose units are then also separated from the remaining insoluble feedstock.

Enzymatic process steps can be combined with one or more pretreatment steps. Such pretreatment step(s) can be unselective to extract components of low commercial value that would otherwise contaminate high-value product streams from the process. Thus, according to one embodiment, one or more of the pretreatment steps are used to extract or otherwise remove defined components. Alternatively, selective one or more pretreatment steps can be used that provide a comparable selectivity to enzymatic process steps in solubilizing individual chemical components of the raw polymeric substrates. Thus, according to one embodiment, one or more pretreatment steps are used to increase the selectivity of the subsequent enzymatic treatment steps. Examples of such process steps would be solubilization of the lignin fraction of LCB by organic solvents such as ethanol or glycerol (Itoh et al., 2003; Demirbas, A., 1998). These individual pretreatment steps and conditions are known to the person skilled in the art. In an additional alternative, said unselective pretreatment steps are applied to insoluble residues, which have been freed from contaminants by previous selective process steps. An example of such a process step is the complete hydrolysis of the protein fraction by acid treatment after selective solubilization of the hemicellulose, cellulose, and lignin fraction of LCB by aforesaid selective process steps.

Another specific example for an embodiment of the invention is given in FIG. 1. Thus, FIG. 1 shows a process flow for the sequential enzymatic processing of LCB.

In this illustration (see FIG. 1) of processing of a substrate rich in cellulose, hemicellulose and lignins and with low amounts of proteins and lipids like wheat straw, corn stover, or softwood, solubilization of the various pentose components contained in the hemicellulose fraction is achieved by sequential treatment with xylanase, arabinase, and mannanase enzymes, which specifically liberate xylose, arabinose, and mannose sugars, respectively. Suitable enzymes and process conditions for providing optimal process conditions for the enzymes are known to the person skilled in the art. The soluble fraction is removed after every process step and the insolubles are contacted with the subsequent enzyme. After processing of the pentose fraction, a similar process step is added to convert cellulose into glucose using a mixture of exo- and endocellulases optionally in combination with cellobiase or beta-glucosidase to liberate glucose and cellobiose from the cellulosic fraction of the LCB substrate. These soluble reaction products are removed from the reaction mixture with the supernatant. Similarly, the lignin fraction remaining in the insoluble phase is converted into its various phenolic building blocks using specific enzyme systems, such as laccases and lignin peroxidases. These phenolic and oligophenolic compounds are then extracted from the reaction mixture with the supernatant or by solvent extraction. Process conditions to perform this process step are known to the person skilled in the art. Each of the individual products resulting from enzymatic conversion of hemicellulose, cellulose, lignin, or other LCB constituents could be isolated after each successive round of enzyme application (see FIG. 1). The resulting, essentially pure chemical building blocks of phenolics, pentose and hexose sugars could then be further processed to high-value commercial products (see FIG. 1). In general, according to one embodiment, the defined monomeric or oligomeric building blocks liberated from the raw or processed polymeric feedstock are purified and optionally further processed.

In another illustration, agricultural residues rich in proteins and lipids such as residues from the production of rape seed, sunflower or olive oils can be contacted subsequently with aforesaid hemicellulases and cellulases and optionally pectinases followed by contacting the residues of this process steps with an unspecific protease. Such unspecific proteases are known to the person skilled in the art and can be produced in large scale. The protease treatment solubilizes amino acid and peptides from the polymeric feedstock. These amino acids and peptides can be subsequently used as a mixture or separated into individual substances by methods known to the person skilled in the art.

In one case the products of interest are arabinose, xylose, glucose, oligophenylpropanoids, monolignols, and/or monophenolics and these products are produced by conversion of the raw polymeric feedstock wheat straw into its component constituents by a sequential enzymatic conversion.

In the primary step of such a sequential process, finely milled wheat straw (1 kg wt, 0.2 µm) with an approximate moisture content of 5% w/w is placed in a steel container. A minimal amount of 2 l water is added and mixed with the feedstock. The resulting slurry is left to soak for 4 h at room temperature. Excess liquid is removed to leave approximately 200 ml of the solution. The container is sealed and heated for 1 h to 121° C. at 10 bar pressure in a conventional sterilizing autoclave system (Puls et al., 1985; Harms, 1989; Foody et al., 1998). The vessel pressure is rapidly released and the content is allowed to cool to room temperature. Under these conditions the polymerization state of the feedstock components is reduced but only a minimal fraction of its components is released in soluble form. The resulting liquid phase (containing salts and minor amounts of various soluble components) and the insoluble phase (containing insoluble polymeric substrates such as cellulose, hemicellulose, and lignin) are separated by way of filtering, sieving, or centrifugation, and the insoluble phase is processed further.

In the next step, in order to mobilize arabinose components contained in the insoluble hemicellulose fraction, a mixture of alpha-L-arabinofuranosidases is applied. All of the reactions mentioned below are performed at a minimum of 40° C. for 24 h in 50 mM phosphate buffer having a pH of 5-7. 0.08-1 g GH51 alpha-L-arabinofuranosidase from *Clostridium thermocellum*/kg of feedstock are added to hydrolyze the alpha-1,2/1,3-arabinofuranosyl moieties of arabinan and xylan (Taylor et al., 2006). Subsequently, 0.08-1 g GH43 alpha-L-arabinofuranosidase from *Humicola insolens*/kg of feedstock are added to hydrolyze the alpha-1,5-arabinofuranosyl units (Sorensen et al., 2006). Because of the specificity of the enzyme mixture, the resulting liquid phase contains mainly arabinose. The released and soluble arabinose units are separated from the insoluble marsh by filtering or centrifugation. The remaining insoluble fraction is retained for further processing.

In the next step, in order to convert insoluble xylan constituents into soluble xylose units, a mixture of xylanases and xylosidases is applied. All of the reactions are performed at a minimum of 40° C. for 24 h in 50 mM phosphate buffer having a pH of 5-7. 0.08-1 g endo-1,4-beta-xylanase (GH10 or 11) from *Humicola insolens*/kg feedstock and 0.08-1 g beta-xylosidase (GH3) from *Trichoderma reesei*/kg of feedstock are added to release xylo-oligosaccharides and xylanose units, respectively. Because of the specificity of the enzyme mixture, the resulting liquid phase contains mainly xylose. The soluble xylose is separated from the insoluble feedstock remains by filtering or centrifugation.

In the next step, in order to mobilize hexose sugars remaining in hemicellulose and cellulosic fractions, the respective insolubles are contacted with an optimized enzyme mixture containing endo- and exocellulases. All reactions are carried out at a minimum of 50° C. for 16 h in 50 mM sodiumacetate buffer (pH 5-6). Mixtures of each 0.005-1 g 1,4-beta-endoglucanases (Cel5A, Cel7B, Cel12A, Cel61A) and 1,4-beta-cellobiohydrolases (Cel7A, Cel6A) from *Trichoderma reesei*/kg insoluble feedstock are added to mobilize hexose sugars (Irwin et al., 1993, Kim et al., 1998). The efficacy and kinetics of cellulose conversion to monomeric sugar units is optionally enhanced by addition of 0.0005-0.01 g cellobiose dehydrogenase from *Phanerocaete chrysosporium* in combination with 0.05-1 g ferrocyanide and 0.0005-0.1 g beta-glycosidase (10% wt enzyme mix) from *Aspergillus niger*/kg feedstock (Igarashi et al., 1998, Rosgaard et al., 2006). Because of the specificity of the enzyme mixture, the resulting liquid phase contains mainly hexoses, predominantly consisting of glucose. These are further separated by way of filtration or centrifugation from the fine particulate remains of the feedstock.

In the next step, insoluble lignin remaining after previous enzyme treatments is converted into its constituents by sequential contact with lignin peroxidase and laccase enzyme systems. Reactions with lignin peroxidase are carried out in a minimum of 50 mM sodium tartrate (pH 3.5) and at a maximum temperature of 32° C. Highly polymeric lignin insolubles are oxidatively decomposed by contacting with each 0.5-1 g of lignin peroxidase (LIP) from *Phanerocaete chrysosporium*/kg of feedstock (Ward et al., 2003). To prevent catalytic inactivation of LIP (Compound III formation, Wariishi and Gold 1990) due to the presence of excess of $H_2O_2$ in the reaction mixture, a soluble enzymatic $H_2O_2$-generating system is used to provide a controlled and continuous environment for $H_2O_2$ formation. The $H_2O_2$-generating power of glyoxal oxidase (GLOX), a natural accessory enzyme working in synergy with lignin peroxidases (Kersten 1990) can be employed. The reaction of GLOX requires the same pH, ionic strength and temperature profile as described for LIP. The generation of $H_2O_2$ is induced by addition of 0.05-1 g GLOX and 0.1-1 g of the GLOX substrate methylglyoxal/kg of feedstock. In order to induce and enhance the oxidative decomposition of polymeric lignin by LIP, the redox mediator veratrylalcohol (3,4-dimethoxybenzyl alcohol) is added to proceed to completion (Ferapontova et al., 2006). A more effective degradation of insoluble lignin can be achieved by adding 2 g veratrylalcohol/kg of feedstock (Barr et al., 1993). The main reaction products of the LIP-catalyzed oxidative decomposition of insoluble lignin are oligophenylpropanoids, while monolignols are only minor components of the product mixture.

In order to increase the amount of monophenolics in the product mixture, the LIP derived product mixture is further reacted with laccase (d'Acunzo et al., 2002). The reaction is carried out at a minimum of 40° C. for 6 h in 100 mM phosphate buffer having a pH of 5-6. 0.0004 g laccase from *Trametes versicolor* and 0.0005 g 2,2,6,6-tetramethylpiperidin-1-yloxy (TEMPO) are added as a redox mediator/kg feedstock (Arias et al., 2003) to oxidize oligophenolics to monophenolic lignin units. Because of the specificity of the enzyme mixture, the resulting liquid phase contains mainly monophenolic lignin units. The resulting product mixture is separated from the remaining marsh by membrane filtration and simple centrifugation.

The following examples show the influence of the sequence of enzymatic treatment steps with different lignocellulosic feedstocks. The examples herein are intended to further illustrate the invention, but shall not be construed to limit in any way the scope of the invention.

Substrate Preparation:

Pretreated Wheat Straw: Dry wheat straw was milled to 120 μm. Then 2 g milled straw was suspended in 39.6 ml dd. Water and 0.4 ml $12NH_2SO_4$ (1% v/v). The suspension was autoclaved at 135° C. for 30 min. The mixture was cooled to RT and centrifuged at 10,000 g for 15 min. The resulting supernatant was discarded. The remaining pellet was worked up with three intermediate washing/centrifugation cycles (10,000 g/15 min) using 50 mM sodium acetate buffer (pH 5). After the final centrifugation step the solid was resuspended in 35 ml of 50 mM sodium acetate (pH 5) giving a 5% w/w (40 g total) substrate stock solution.

Untreated wheat straw, sugarbeet pulp, oat spelt xylan, rye arabinoxylan: Dry samples of wheat straw (local agricultural produce), sugarbeet pulp (animal feed additive), oat spelt xylan (Sigma, Weilheim, Germany, Cat no: X0627) were milled to 120 μm. For the preparation of individual substrate stock solutions 2 g of each milled material was placed in a Flacon tube. The tube was then filled with 50 mM sodium acetate buffer (pH 5) up to the 40 g mark giving a final substrate suspension of 5% (w/w).

Rye Arabinoxylan (Megazymes, Ireland, Cat no: P-RAXY) was supplied as white fine powder. For the preparation of the substrate stock solution 0.2 g was weight into a Flacon tube (15 ml). The tube was then filled with 50 mM sodium acetate buffer up to the 4 g mark to give a final stock solution of 5% (w/w).

Enzyme Preparation:

Arabinase (Ara, Source: *A. niger*, Cat.: E-EARAB), arabinofucosidase (Arafus, Source: *A. niger*, Cat.:E-AFASE), cellobiohydrolase I (CBH I, Source: *Trichoderma* sp., Cat.: E-CBHI), endo-β-D-glucanase (EGII, Source: *Trichoderma* sp., Cat.: E-CELTR), endo-β-Mannanase (Man, Source: *A. niger*, Cat: E-BMANN), Xylanase (Xyl 1, Source: *T. viride*; Cat. E-XYTR1), polygalacturonase (Poly, Source: *A. aculeatus*, Cat.E-PGALUSP) were supplied by Megazymes Inc., Ireland as ammonium sulphate precipitates (total volume: 1 ml). These enzyme preparations were desalted and concentrated with 45 ml sodium acetate buffer (50 mM, pH 5) using 50 ml Amicon centrifugal ultrafiltration devices (10 kDa cut-off; Millipore, Maidstone, UK).

A commercial cellulase mixture (Worth. Cel., Cat: Cel; 108 U/mg DW) containing, cellobiohydrolase (CBH I and CBH II), endocellulase (EG I, EG II), β-glycosidase (BGL) and endo-xylanase activities was supplied by Worthington Biochemical Corp. (NJ., USA) as a dry white powder. Stock solutions of this cellulase preparation (0.5 mg/ml) were made up in 10 ml sodium acetate buffer, (50 mM, pH 5).

Pectinase (Pec, Activites: pectate lyase, polygalactouronase; Cat: Pectinex Ultra SP-L) from *A. aculeatus* and β-glucosidase from *A. niger* (BGL, Cat: Novo 188) was supplied as a concentrated solution ready for use by Novozymes, Denmark.

An additional endo-xylanase activity (Xyl 2, BLAST reference: AAZ56956/gi:71917054; http://www.ncbi.nlm.nih.gov/sites/entrez) from Thermobifida fusca strain YX was recombinantly expressed in *S. cerevisiae*. The enzyme activity was obtained from clarified and concentrated fermentation broth using Amicon centrifugal ultracentrifugation devices (Millipore, Maidstone, UK).

Protein concentrations were determined by the Bradford method (Bradford, M., 1976).

Preparation of Hydrolysis Lignin:

Wheat straw (300 g) was pretreated using a conventional steam explosion methodology (25 bar steam/5 min with sudden pressure release) in the presence of 1% (w/v) $12N H_2SO_4$. The resulting suspension was centrifuged at 10.000 g (15 min.) and the supernatant decanted. The remaining solid was washed/neutralized three times with 40 ml sodium acetate buffer (50 mM, pH 5) before it was dried in-vacuo and subsequently milled to 120 μm giving a fine powder. To prepared a 5% (w/w) suspension, 2 g of the straw powder was mixed with 35 ml sodium acetate buffer (50 mM, pH5) giving a total volume of 40 ml. The 40 ml straw suspension was mixed with 4% (w/w Substrate) Worthington cellulase mixture and 0.5% (w/w) β-glycosidase activity from *Aspergillus niger* (Novo 188, Novozymes). The resulting mixture was incubated at 45° C. (250 rpm) for 48 h in an Eppendorf rotary mixer. After the initial incubation period the suspension was centrifuged at 12.000 g (15 min) and the resulting supernatant was decanted. The remaining solid was washed twice with d.d water centrifuged (12.000 g/15 min) and resuspended in sodium acetate buffer (50 mM, pH5) giving a final volume of 40 ml. The suspension was again mixed with 4% (w/w Substrate) Worthington cellulase mixture and 0.5% (w/w) β-glycosidase from *Aspergillus niger* (Novo 188, Novozymes) before it was incubated for an additional 24 h period at 45° C. After this secondary incubation period the solid was separated by centrifugation as described previously. The solid was again washed twice with d.d water and subsequently centrifuged (10,000 g/15 min) to separate liquid and solid phases. The resulting solid was then dried in-vacuo for 24 h giving the hydrolysis lignin fraction (374 mg) used for following experimental sets. To ensure that the lignin obtained by this methodology did not retain any residual sugars, 50 mg of the obtained solid was subjected to total acid catalysed hydrolysis according to published NREL protocols (5). The presence of possible sugar components was tested by High-Performance Anion Exchange chromatography combined with Pulsed Amperometric Detection (HPAE-PAD) analysis (Dionex, Ca., USA, 6). Although this methodology is more sensitive (~1000 fold) than standard HPLC protocols, no residual sugars could be detected in the hydrolysis lignin residue obtained here.

Sequential Enzymatic Hydrolysis Experiments:

All reactions were carried out in a total volume of 0.5 ml with a sodium acetate buffer (50 mM, pH 5) system. Positive controls consisted of a single enzymatic hydrolysis step for each substrate (2.5% w/v=25 mg/ml) using the Worthington cellulase mixture (1% w/w substrate=0.25 mg/ml). The following sequential hydrolysis reactions of various substrates were carried out in two independent steps.

The initial substrate concentration for primary hydrolysis reactions was 2.5% (w/v), while the total enzyme concentration was 1% (w/w substrate) held constant in each reaction. The mass distribution of sugar components in the individual substrate is evident from Table 1A. Each enzymatic reaction was incubated at 45° C./250 rpm for 48 h in an Eppendorf rotary mixer. After primary hydrolysis, the suspension was centrifuged at 10,000 g for 15 min. The supernatant was decanted, filtered (0.2 μm) and subjected to HPAE-PAD analysis (Dionex, Ca., USA, 6) to determine its sugar and uronic acid composition.

The pellet remaining after primary hydrolysis was resuspended in 1 ml water and centrifuged (10,000 g/15 min). After centrifugation the water wash was discarded and the pellet (~100 ml volume) used for secondary hydrolysis experiments. The enzyme concentration added in the secondary hydrolysis set-up was 1% w/w (0.25 mg/ml) with respect to the initial substrate concentration. After enzyme addition, the reaction volume was made up 0.5 ml with sodium acetate buffer. For the secondary hydrolysis step different enzymatic activities were used then in the primary reaction step. However, in cases where industrial enzyme mixtures were used, minor enzyme activity, that were equivalent to the primary reaction step could be tolerated. After the 48 h incubation period the hydrolysis suspension was centrifuged at 10,000 g for 15 min. The supernatant was processed as previously described and subjected to HPAE-PAD analysis (Dionex, Ca., USA, 6) to determine its sugar and uronic acid composition.

The exact combinations of enzymes and substrates used for primary and secondary hydrolysis step for each substrate are listed in Table 2A.

The following list contains enzyme concentrations/combinations for individual reactions:

1.) Arabinase (Ara: 0.2 mg/ml)+Arabinofucosidase (Arafus: 0.05 mg/ml)
2.) CBH I (0.175 mg/ml)+EG II (0.005)+BGL (0.025 mg/ml)
3.) Mannanase (Man: 0.25 mg/ml)
4.) Polygalacturonase (Poly: 0.25 mg/ml)
5.) Pectinase (Pec: 0.25 mg/ml)
6.) Xylanase (Xyl1 or Xyl 2: 0.25 mg/ml)
7.) Xylanase (Xyl 1 or Xyl 2: 0.2 mg/ml)+β-glycosidase (BGL: 0.05 mg/ml)
8.) Worthington (0.25 mg/ml)

For reactions carried out with pretreated straw and beet pulp, the appropriate xylanase primary or secondary hydrolysis steps were carried out exclusively with Xyl 1 derived from a *Trichoderma viride*.

By contrast all other xylanase hydrolysis steps were carried out with Xyl 2 derived from Thermobifida fusca strain YX.

TABLE 1A

Mass (%) distribution of substrate components determined after quantitative acid hydrolysis (1-4)

| Substrate | Glucose | Arabinose | Xylose | Other components |
|---|---|---|---|---|
| Oat spelt Xylan | 15 | 10 | 70 | 5 |

| | Arabinose | Xylose | Other sugars |
|---|---|---|---|
| Rye ArabinoXylan | 38 | 59 | 3 |

| | Extractives | Ash | Total Lignin | Uronic acid | Arabinan | Xylan | Mannan | Galactan | Cellulose | Other componenets |
|---|---|---|---|---|---|---|---|---|---|---|
| untreated Straw | 12.95 | 10.22 | 16.85 | 2.24 | 2.35 | 19.22 | 0.31 | 0.75 | 32.64 | 2.47 |

| | Glucose | Galactose | Mannose | Rhamnose | Xylose | Arabinose | Galacturonic acid | Actetic acid | Lignin | Other componenets |
|---|---|---|---|---|---|---|---|---|---|---|
| Beet pulp | 25 | 7 | 1 | 3 | 2 | 25 | 23 | 4 | 1.5 | 8.5 |

| | Glucose | Xylose | Lignin | Other Components |
|---|---|---|---|---|
| Pretreated straw | 70 | 3 | 21 | 6 |

TABLE 2A

Sequential hydrolysis steps carried out with various substrates

| Experimental set | relative distribution of Analyte (%) | | | | | |
|---|---|---|---|---|---|---|
| | Glucose | Xylose | Arabinose | Galactose | Oligosaccharides | Uronic acid |
| *Straw untreated* | | | | | | |
| 1.1.1 Ara + Arafus | 0.766 | 1.278 | 93.888 | 0.000 | 1.066 | 3.002 |
| 1.1.2 CBH I + EG II + BGL | 95.031 | 1.589 | 0.067 | 1.064 | 0.294 | 1.954 |
| 1.2.1 CBH I + EG II + BGL | 74.930 | 14.601 | 10.507 | 0.469 | 0.047 | 0.063 |
| 1.2.2 Ara + Arafus | 8.213 | 4.710 | 85.583 | 0.000 | 1.095 | 0.399 |
| Positive control | 83.855 | 12.193 | 0.118 | 1.044 | 1.588 | 1.201 |
| *Rye Arabinoxylan* | | | | | | |
| 2.1.1 Ara + Arafus | 0.000 | 20.476 | 79.524 | 0.000 | 0.000 | 0.000 |
| 2.1.2 Xyl 2 | 0.000 | 92.973 | 2.341 | 0.000 | 0.403 | 4.279 |
| 2.2.1 Xyl 2 | 1.670 | 70.141 | 26.330 | 0.609 | 1.189 | 0.053 |
| 2.2.2 Ara + Arafus | 0.000 | 20.476 | 79.524 | 0.000 | 0.000 | 0.000 |
| Positive control | 0.000 | 54.305 | 30.022 | 0.000 | 0.414 | 15.259 |

| Experimental set | relative distribution of Analyte (%) | | | | | |
|---|---|---|---|---|---|---|
| | Arabinose | Galactose | Glucose | Xylose | Mannose | Oligosaccharides |
| *Beet samples* | | | | | | |
| 3.1.1 Ara + Arafus | 76.956 | 1.000 | 1.044 | 0.000 | 0.000 | 19.660 |
| 3.1.2 CBH I + EG II + BGL | 1.604 | 1.354 | 83.458 | 3.772 | 8.050 | 0.517 |
| 3.2.1 Ara + Arafus | 76.956 | 1.000 | 1.044 | 0.000 | 0.000 | 19.640 |
| 3.2.2 Worth Cel. Mix | 1.725 | 0.967 | 89.233 | 3.783 | 2.977 | 0.357 |
| 3.3.1 CBH I + EG II + BGL | 3.886 | 2.094 | 61.191 | 32.108 | 0.406 | 0.006 |
| 3.3.2 Ara + Arafus | 61.827 | 0.000 | 34.127 | 1.457 | 0.000 | 0.135 |
| Positive control | 2.347 | 0.000 | 85.252 | 4.229 | 0.160 | 1.310 |
| *Pretreated Straw samples* | | | | | | |
| 4.1.1 Xyl1 | 0.735 | 1.907 | 6.842 | 87.328 | 0.000 | 3.120 |
| 4.1.2 CBH I + EG II + BGL | 0.000 | 0.364 | 95.398 | 3.076 | 0.439 | 0.721 |
| 4.2.1 Xyl 1 | 0.735 | 1.907 | 6.842 | 87.328 | 0.000 | 3.150 |
| 4.2.2 Pectinase | 0.000 | 1.700 | 93.490 | 1.991 | 2.508 | 0.310 |
| 4.3.1 Xyl 1 | 0.735 | 1.907 | 6.842 | 87.328 | 0.000 | 3.110 |
| 4.3.2 Ara + Arafus | 0.000 | 0.000 | 94.849 | 5.153 | 0.000 | 0.000 |
| 4.4.1 CBH I + EG II + BGL | 0.500 | 0.435 | 74.398 | 16.676 | 1.339 | 6.042 |
| 4.2.1 Xyl1 | 0.040 | 0.364 | 22.398 | 73.076 | 0.439 | 3.721 |
| Positive control | 0.000 | 0.000 | 89.136 | 3.684 | 0.000 | 5.452 |

As positive Control: Worthington (Worth. Cel.) was used.

By comparing the data in Table 2A it is evident that by choosing the right combination of enzymatic steps, pure sugar product streams in excess of 80% (w/w) can be obtained from the hydrolysis of lignocellulosic substrates.

It is also evident that the sequence of enzymatic activities applied to a specific hydrolysis substrate has a profound influence on the composition and purity of the resulting product streams.

In a further set of experiments the influence of the presence of lignin in the feedstock on the enzymatic treatment steps was investigated:

Selective Enzymatic Hydrolysis in the Absence/Presence of Hydrolysis Lignin:

All reactions were carried out in a total volume of 0.5 ml with a sodium acetate buffer (50 mM, pH 5) system in 1 ml Eppendorf tubes. Suspensions containing 2.5% (w/v) untreated wheat straw (25 mg/ml) or rye arabinoxylan (0.25 mg/ml) were hydrolysed with 1% (w/w substrate=0.25 mg/ml) of either endo-arabinase (Ara), endo-polygalacturonase (Poly) or endo-xylanase (Xyl 2). Each reaction was carried out either in the absence or presence of 2.5% (25 mg/ml) additional hydrolysis lignin. The substrate to lignin ratio in the respective reactions was therefore 1:1. All reactions were incubated for 48 h at 45° C. (250 rpm) in an Eppendorf rotary mixer. After the incubation period, the samples were centrifuged at 10,000 g for 15 min. The resulting supernatant was removed by pipetting to determine its sugar and uronic acid composition using the HPAE-PAD methodology (6). The results shown in table 3 only concentrate on changes in hydrolysis patterns of the major monomeric sugar components.

Table 3: Selective Hydrolysis of Arabinoxylan and Untreated Straw in the Absence/Presence of Additional Lignin.

a.) Results Obtained for Arabinoxylan

| | rel. distribution (%) | | |
|---|---|---|---|
| Experimental set | Glucose | Xylose | Arabinose |
| Xyl 2 + Lignin | 0.12 | 95.63 | 4.27 |
| Xyl 2 − Lignin | 0.28 | 78.09 | 21.65 | b.) Results Obtained for Untreated Straw

| | rel. distribution (%) | | |
|---|---|---|---|
| Experimental set | Glucose | Xylose | Arabinose |
| Xyl 2 + Lignin | 0.19 | 97.50 | 2.16 |
| Xyl 2 − Lignin | 4.31 | 84.50 | 12.10 |

We have chosen rye arabinoxylan (Endogenous lignin content<0.2% w/w) and untreated wheat straw (Endogenous lignin content ~17% w/w) as hydrolysis substrates to study the effects of exogenous lignin addition since these substrates differ significantly in their endogenous lignin content.

In the presence of exogenous lignin the hydrolysis of arabinoxylan and untreated wheat by endo-xylanase 2 (Xyl 2) resulted in a significant product selectivity increase. For both substrates the endo-arabinase side activity of Xyl 2 was reduced in the presence of lignin.

Citations:
1.) http://www.eere.energy.gov/biomass/progs/search2.cgi?4669
2.) Michel, F. et al. (2006), J. of the Science of Food and Agriculture 42 (1), pp. 77-85
3.) http://secure.megazyme.com/Dynamic.aspx? control=CSViewProduct&categoryName=Polysaccharides&productid=P-RAXY
4.) www.sigma.com
5.) http://www.nrel.gov/biomass/pdfs/42618.pdf
6.) http://www.dionex.com.cn/technic/Afiles/AN92. PDF Literature Hamsen, G. et al. (1989) Process for the treatment of biomass with steam, product thereby obtained and its use and reactor. EP 0187422A2

Chen, W. P., Matsuo, M., Yasui, T. (1986) Agric. Biol. Che. 50, pp. 1183-1194

Arias, M. E., Arenas, M., Rodriguez, J., Solviveri, J., Ball, A. S., Hernandez, M. (2003) Kraft pulp biobleaching and mediated oxidation of a non-phenolic substrate by laccase from *Streptomyces cyaneus* CECT 3335. Appl. Envir. Microbiol. 69, pp. 1953-1958

D'Acunzo, F. Galli, C., Masci, B. (2002) Oxidation of phenols by laccase and laccase-mediator systems. Solubility and steric issues. Eur. J. biochem. 269, pp. 5330-5335

Barr, D., Sha, M. M., Aust, S. D. (1993) Veratrylalcohol-dependent production of molecular oxygen by Lignin peroxidase. J. Biol. Chem. 268, pp. 241-244

Currie, H. A., Perry, C. C. (2006) Resolution of complex monosaccharide mixtures from plant cell wall isolates by high pH anion exchange chromatography. J. Chromatography. 1128 (1-2), pp. 90-96

Demirbas, A. (1998) Aqueous glycerol delignification of wood chips and ground wood. Bioresource Technol. 63 (2), pp. 179-185

Irwin, D. C., Spezio, M., Walker, L. P., Wilson, D. B. (1993) Biotech. Bioengineer. 42, pp. 1002-1013.

Itoh, H., Wada, M., Honda, Y., Kuwahara, M., Watanabe, T. (2003) Bioorganosolve pretreatments for simultaneous saccharification and fermentation of beech wood by ethanolysis and white rot fungi. J. Biotechnol. 103, pp. 273-280

Igarashi, K., Samejima, M. Eriksson, K.-L. (1998) Cellobiose dehydrogenase enhances *Phanerocaete chrysosporium* cellobiohydrolase I activity by relieving product inhibition. Eur. J. Biochem. 253, pp. 101-106

Ferapontova, E. E., Castillo, J., Gorton, L. (2006) Bioelectrocatalytic properties of lignin peroxidase from *Phanerocaete chrysosporium* in reactions with phenols, catechols and lignin-model compounds. Biochem. Biophys. Acta 1760 (9), pp. 1343-54

Foody, B. et al. (1998) Pretreatment process for the conversion of cellulose to fuel ethanol. U.S. Pat. No. 6,090,595

Kamm, B., Gruber, P. R., Kamm, M. (2006) Industrial processes and products Status quo and future direction. Biorefineries 1, pp. 1-39

Kamitsuiji, H., Watanabe, T., Honda, Y., Kuwahara, M. (2005) Direct oxidation of polymeric substrates by multifunctional manganese peroxidase isoenzyme from *Pleurotus ostreatus* without redox mediators. Biochem. J. 386, pp. 387-393.

Kaschemekat, J. Klose, M. (1985) Trennung der Komponenten eines Flussigkeitsgemisches. DE 3410155C1

Kersten, P. J. (1990) Glyoxal oxidase of *Phanerocaete chrysosporium*: its characterization and activation by Lignin-peroxidase Proc. Natl. Acad. Sci. 87, pp. 2936-2940

Kim, E., Irwin, D. C., Walker, L. O., Wilson, D. B. (1998) Factorial optimisation of a six-cellulase mixture. Biotech. Bioengineer. 58(5), pp. 494-501

Kinley, M. T, Krohn, B. Biomass conversion to alcohol using ultrasonic energy. US 200570136520A1

Lawford, H. G., Rousseau, J. D. (2003) Cellulosic fuel ethanol. Appl. Biochem and Biotechnol. 105, pp. 457-469

Lawford, H. G., Rousseau, J. D. (2003) Cellulosic fuel ethanol. Alternative fermentation process designs with wild-type and recombinant *Zymomonas mobilis*. Appl. Biochem. Biotechnol. 105, pp. 457-469

Lynd, L. R., van Zyl, W. H.v., McBride, J. E., Laser, M. (2005) Consolidated bioprocessing of cellulosic biomass: an update. Curr. Opin. Biotechnol. 16, pp. 577-583

Mammela, P. (2001) Phenolics in selected European hardwood species by liquid chromatography-electrospray ionization mass spectrometry. Analyst 126(9), pp. 1535-1538

Palla, G. (1981) C18 reversed-phase liquid chromatography determination of invert sugar, sucrose and raffinose. Anal. Chem. 53, pp. 1966-1967

Puls, J., Poutanen, K., Körner, H.-U., Viikari, L. (1985) Biotechnological utilization of wood carbohydrates after steaming pretreatment. Appl. Microbiol. Biotechnol. 22, pp. 416-423

Ramos, L. P., Silva, T. A., Martins, L. F., Satyanarayana, K. G. (2005) Conversion of lignocellulosics to fules, chemicals and environmentally-friendly materials. Metals and Processes 117, pp. 299-318

Rosgaard, L., Peterson, S., Chemy, J. R., Harris, P., Meyer, A. S. (2006) Efficiency of new fungal cellulose systems in boosting enzymatic degradation of barley straw lignocellulose. Biotechnol. Prog. 22(2), pp. 493-498

Saha, B. C., Enzymes as biocatalysts for conversion of lignocellulosic biomass to fermentable sugars (2005) in Handbook of industrial biocatalysis, ed. Ching T. Hou, CRC Press, Chapter 24, pp. 1-12

Smirnov, S. A., Korovela, O. V., Gavrilova, V. P., Belova, A. B., Klyachko, N. L. (2001) Laccases for basidomyces: Physicochemical characteristics and substrate specificity towards methoxyphenolic compounds. Biochem. (Moscow) 66(7), pp. 774-779

Sorensen, H., Pederson, S., Viksoe-Nielsen, A. et al. (2006) Hydrolysis of arabinoxylan. WO 2006114095A1

Taylor, E. Smith, N., Turkenburg, J. et al. (2006) Structural insights into the ligand specificity of a thermostable family 51 arabinofuranosidase, Araf51, from *Clostridium thermocellum*. Biochem. J. 395, pp. 31-37

Ward, G., Hadar, Y., Bilkis, I., Dosoretz, C. (2003) Mechanistic features of lignin peroxidase-catalysed oxidation of substituted phenols and 1,2-dimethoxyarenes. J. Biol. Chem. 278, pp. 39726-39734

Wariishi, H., Gold, M. H. (1990) Lignin Peroxidase Compound II. Mechanism of formation and decomposition. J. Biol. Chem. 265, pp. 2070-2077

Wood, T. M. and Baht, K. M., Methods for measuring cellulose activities. Methods in Enzymology. 160, pp. 87-112

TABLE 1

| Product | Polymeric Substrate | Enzyme activity | Enzyme mixture numbers |
|---|---|---|---|
| 1-Acylglycerophosphocholine | Phosphatidylcholine | Phospholipase | 1 |
| 1,5-Anhydro-D-fructose + D-glucose | Alpha-glucan | Exo-alpha-1,4-D-glucan lyase | 1 |
| Alcohol + acetate | Xyloglucan Rhamnogalacturonan | Acetylesterase | 1 |
| Amino acids | Proteins | Protease | 1 |
| Arabinose | Arabinan | Arabinofuranosidase | 2, 5 |
|  | Arabinoxylan | Endo-alpha-1,3-L-arabinanase | 1, 3, 4 |
|  | Xyloglucan | Endo-alpha-1,5-L-arabinanase | 1 |
|  |  | Exo-alpha-1,3-L-arabinanase | 1, 2, 3 |
|  |  | Exo-alpha-1,5-L-arabinanase | 1, 2, 5 |
| Choline | Acetic esters | Acetylcholinesterase | 1, 2 |
|  | Choline esters | Cholinesterase | 1, 3 |
| D-Xylonate | Xylono-1,4-lactone | Xylono-1,4-lactonase | 1 |
| Diacylglycerol | Triglyceridester | Triacylglycerol lipase | 1 |
| Fucose | Xyloglucan | Endo-alpha-1,2-L-fucosidase | 1, 2 |
|  |  | Exo-alpha-1,2-L-fucosidase | 1, 2, 3, 4 |
|  | Pectin | Pectinase | 1, 3 |
| Galactose | Galactan | Endo-beta-1,4-D-galactosidase | 1 |
|  | Galactomannan | Exo-beta-1,4-D-galactosidase | 1, 2 |
|  | Xyloglucan |  |  |
| Gallate | Digallate | Acylglycerol lipase | 1, 3 |
|  | Glycerol monoesters of long-chain fatty acids | Tannase | 1, 2 |
| Glucose | Cellulose | Cellulase | 1, 2, 3, 4, 5, 6, 7, 8 |
|  | Glucomannan | Alpha-amylase | 1, 2, 3, 4, 6 |
|  | Glucoronoxylan | Beta-amylase | 1, 2, 3, 5, 6 |
|  | Xyloglucan | Beta-glucosidase | 1, 2, 3, 4, 6 |
|  |  | Cellobiohydrolase I | 1, 3, 4, 6, 7 |
|  |  | Cellobiohydrolase II | 2, 3, 4, 6, 8 |
|  |  | Endo-beta-1-4-D--glucanase | 1, 2, 3, 4, 5, 6 |
|  |  | Endoglucanase I | 1, 2, 4, 6 |
|  |  | Endoglucanase II | 1, 2, 4, 5, 6 |
|  |  | Endoglucanase III | 1, 2, 3, 5, 6 |
|  |  | Endoglucanase IV | 1, 2, 3, 5, 6 |
|  |  | Endoglucanase V | 1, 3, 4, 6 |
|  |  | Endoglucanase VI | 1, 3, 4, 6 |
|  |  | Endoglucanase VII | 1, 3, 4, 6 |
|  |  | Exo-beta-1,4-D-glucanase | 1, 2, 3, 4, 5, 6, 7, 8 |
|  |  | Glucohydrolase | 1, 2, 3, 4, 6 |
| Glucose | Starch | Alpha-amylases | 1, 2 |
|  |  | Beta-amylases | 1, 3 |
| Glycerophosphocholine | 2-Lysophosphatidylcholine | Lysophospholipase | 1 |
| L-Arabinonate | L-Arabinono-1,4-lactone | L-Arabinonolactonase | 1 |
| Long-chain alcohol | Wax ester | Wax-ester hydrolase | 1 |
| Long-chain-fatty acid | Long-chain-fatty-acyl ethyl ester | Fatty-acyl-ethyl-ester synthase | 1 |
| Mannose | Galactomannan | Beta-1,4-D-mannosidase | 2 |
|  | Mannan | Endo-beta-1,4-D-mannanase | 1 |
|  |  | Exo-beta-1,4-D-mannanase | 1, 2, 3 |
| Methanol + pectate | Pectin | Pectinesterase | 1, 2, 3 |
|  |  | Pectin demethoxylase | 1 |
|  |  | Pectin methoxylase | 1, 2 |
| Oligolignan, monolignole, phenolic compounds, | Lignin | Laccase (TEMPO) | 1, 2, 6 |
|  |  | Lignin peroxidase | 1, 3, 4 |

TABLE 1-continued

Enzyme systems

| Product | Polymeric Substrate | Enzyme activity | Enzyme mixture numbers |
|---|---|---|---|
| oligophenylpropanoids | | (Veratrylalcohol) + Glyoxal oxidase (primary aldehydes or methylglyoxal) | |
| | | Manganese peroxidase ($Mn^{2+}$ organic acids) | 1, 2, 3, 5 |
| Oligopeptides | Proteins | Amino-peptidase | 1, 2, 8 |
| | | Carboxy-peptidase | 1, 3, 8 |
| | | Carboxyl-proteinase | 1, 4 |
| | | Endo-peptidase | 1, 4, 5, 6, 7 |
| | | Exo-peptidase | 1, 2, 3, 8 |
| | | Metallo-proteinase | 1, 5 |
| | | Serin-proteinase | 1, 6 |
| | | Thiol-proteinase | 1, 7 |
| Oligosaccharides with terminal 4-deoxy-alpha-D-galact-4-enuronosyl groups | Alpha-1,4-D-galacturonan | Pectate lyase (alpha-1,4-D-endopolygalacturonic acid lyase) | 1 |
| Phytol | Chlorophyll | Chlorophyllase | 1 |
| Ribonucleotides | RNA | Endoribonuclease | 1, 2, 3 |
| | | Exoribonuclease | 1, 2, 4, 5 |
| | | Ribonuclease | 1, 3, 4, 5 |
| Sterol | Steryl ester | Sterol esterase | 1, 2 |
| | | Triterpenol esterase | 1, 3 |
| Uronic acids | Pectin | Polygalacturinase | 1 |
| | | Pectin lyase | 1, 2 |
| Xylose | Arabinoxylan | Endo-beta-1,3-D-xylanase | 1, 3, 6 |
| | Glucoronoxylan | Endo-alpha-1,6-D-xylosidase | 1, 2 |
| | Xylan | Endo-beta-1,4-D-xylanase | 1, 2, 3 |
| | Xyloglucan | Exo-alpha-1,6-D-xylanase | 1, 2, 7 |
| | | Exo-beta-1,3-D-xylanase | 1, 3, 5, 6 |
| | | Exo-beta-1,4-D-xylanase | 1, 2, 3, 4 |
| | | Xylosidase | 1, 2, 3 |

Exemplary enzyme combinations for the generation of a specific product obtained from a specific polymeric feedstock constituent are denoted individually by numbers ranging from 1 to 8.

TABLE 2

| Substrate | Sigma Cat. Number | Enzyme | Product |
|---|---|---|---|
| Cellulose | C6288 | Endo-cellulase, Exo-cellulase, β-Glycosidase | Glucose |
| Cellodextrins | C4642 | Endo-cellulase, Exo-cellulase, β-Glycosidase | Glucose |
| β-Methlylumbelliferyl-oligosacharides | M6018 | Endo-cellulase, Exo-cellulase, β-Glycosidase | Glucose |
| p-Nitrophenol-oligosaccharides | N0145 | Endo-cellulase, Exo-cellulase, β-Glycosidase | Glucose |
| CMC | C9481 | Endocellulase | Oligoscaccharides |
| Avicel PH-101 | 11365 | Exocellulase | Glucose |
| 4-Nitrophenyl-β-D-cellobioside | N5759 | | Glucose and pNP |
| Xylan | X4252 | Xylanase, xylanosidase | Xylose |
| 4-Nitrophenyl-β-D-xylopyranoside | N2132 | Cellulase | Xylose and pNP |
| Mannan from yeast | M7504 | Mannanase | Mannanoside and mannose |
| D-Galacto-D-mannan from *Ceratonia siliqua* | 48230 | Galactase and mannanase | Galactose and mannose |
| 4-Nitrophenyl α-L-arabinofuranoside | N3641 | Arabinofucosidase | Arabinose and pNP |
| 2,3-Dimethoxybenzyl alcohol (veratrylalcohol) | 38700 | Lignin peroxidase (LIP) | Veratrylalcohol radical cation |
| Lignin, hydrolytic | 371076 | Lignin peroxidase (LIP) | Phenylpropanoids |
| Lignin, organosolv | 371017 | Lignin peroxidase (LIP) | Phenylpropanoids |
| 2,2'-Azino-bis(3-ethylbenzothiazoline-6-sulfonic acid (ABTS) | A1227 | Lignin peroxidase (LIP) | ABTS radical cation |
| 2,2'-Azino-bis(3-ethylbenzothiazoline-6-sulfonic acid (ABTS) | A1227 | Laccase | ABTS radical cation |
| Manganesechloride ($MnCl_2$) | 416479 | Manganeseperoxidase (MnP) | $Mn^{3+}$ ion |

What is claimed is:

1. A method for the enzymatic treatment of raw polymeric feedstock comprising soluble and insoluble components, the method comprising:
   a. treating the insoluble raw polymeric feedstock with an enzyme system in order to liberate defined soluble monomeric or oligomeric building blocks from the raw polymeric feedstock; and
   b. separating the defined soluble monomeric or oligomeric building blocks produced in a) from the remainder of the insoluble raw polymeric feedstock, wherein the raw polymeric feedstock comprises at least 1 wt-% lignin, and
   wherein a) and b) are sequentially repeated one or more times with different enzyme systems in order to liberate from the remainder of the raw polymeric feedstock other defined soluble monomeric or oligomeric building blocks, and
   wherein the enzyme system used in a particular enzymatic treatment contains not more than 20% of contaminating enzymatic activities, which can cause liberation of other defined monomeric or oligomeric building blocks, which have not been liberated in previous enzymatic treatments.

2. The method of claim 1, wherein the raw polymeric feedstock comprises at least 10 wt-% lignin.

3. The method of claim 1, wherein no ligninolytic enzyme treatment is performed.

4. The method of claim 1, wherein the content of lignin in the polymeric feedstock, calculated as wt-% of the overall composition of the polymeric feedstock is not reduced during a) and b) or their repetition.

5. The method of claim 1, wherein prior to a) soluble components are separated from the raw polymeric feedstock.

6. The method of claim 5, wherein the separation of soluble components from the raw polymeric feedstock is performed using one or more washings and/or and one or more physico-chemical treatments.

7. The method of claim 1, wherein the enzyme system used in a) contains not more than 5% of contaminating enzyme activities apart from an enzyme activity resulting in liberation of said defined soluble monomeric or oligomeric building blocks from the insoluble raw polymeric feedstock according to a).

8. The method according to claim 1, wherein prior to the second enzymatic treatment of a), the method further comprises separating the soluble components from the processed polymeric feedstock using one or more pretreatments, optionally one or more washings.

9. The method of claim 1, wherein the enzymatic treatment is performed in an aqueous medium, said defined monomeric or oligomeric building blocks liberated from the raw or processed polymeric feedstock are soluble in the aqueous medium and the separation according to b) is performed by liquid/solid separation of the soluble building blocks in the aqueous medium from the remainder of the insoluble raw or processed polymeric feedstock.

10. The method of claim 1, wherein the defined monomeric or oligomeric building blocks according to a) are chosen from one of the group consisting of glucose, xylose, arabinose, galactose, mannose, amino acids and phenolic compounds.

11. The method of claim 1, wherein the feedstock is a cellulose-xylan-rich feedstock and wherein the enzyme or enzyme system used in the first enzymatic treatment of a) is a glucose-liberating enzyme or enzyme system, and the defined soluble monomeric or oligomeric building block is glucose, and wherein the enzyme or enzyme system used in the second enzymatic treatment of a) is a xylose-liberating enzyme or enzyme system, and the defined soluble monomeric or oligomeric building block is xylose.

12. The method according to claim 1 wherein the enzyme or enzyme system used in the first treatment of a) is selected from the group consisting of Beta-glucosidase from *A. niger* or *T. reesei*; Cellobiohydrolase I-II from *T. reesei*, and Endo-beta-1-4-D -glucanase I-V from *T. reesei*, and wherein the enzyme or enzyme system used in the second treatment of a) is selected from the group consisting of Endoxylanase from *A. niger* or *T. reesei* or *C. thermocellum*; and Xylosidase from *A. niger* or *T. reesei*.

13. The method of claim 1, wherein the feedstock is a cellulose-xylan-rich feedstock and wherein the enzyme or enzyme system used in the first enzymatic treatment of a) is a xylose-liberating enzyme or enzyme system, and the defined soluble monomeric or oligomeric building block is xylose, and wherein the enzyme or enzyme system used in the second enzymatic treatment of a) is a glucose-liberating enzyme or enzyme system, and the defined soluble monomeric or oligomeric building block is glucose.

14. The method of claim 1, wherein the enzyme or enzyme system used in the first treatment of a) is selected from the group consisting of Endoxylanase from *A. niger* or *T. reesei* or *C. thermocellum*, and Xylosidase from *A. niger* or *T. reesei*, and wherein the enzyme or enzyme system used in the second treatment of a) is selected from the group consisting of Beta-glucosidase from *A. niger* or *T. reesei*; Cellobiohydrolase I-II from *T. reesei*, and Endo-beta-1-4-D -glucanase I-V from *T. reesei*.

15. The method of claim 1, wherein the feedstock is an arabinan-pectin-rich feedstock and wherein the enzyme or enzyme system used in the first enzymatic treatment of a) is a arabinose-liberating enzyme or enzyme system, and the defined soluble monomeric or oligomeric building block is arabinose, and wherein the enzyme or enzyme system used in the second enzymatic treatment of a) is a uronic acid-liberating enzyme or enzyme system, and the defined soluble monomeric or oligomeric building block is uronic acid.

16. The method of claim 1, wherein the enzyme or enzyme system used in the first treatment of a) is selected from the group consisting of Endoarabinase from *A. niger* and Arabinofucosidase from *A. niger*, and wherein the enzyme or enzyme system used in the second treatment of a) is a Pectinase from *A. aculeatus, A. niger* or *C. japonicus*.

17. The method of claim 1, wherein the feedstock is an arabinan-pectin-cellulose-rich feedstock and wherein the enzyme or enzyme system used in the first enzymatic treatment of a) is an arabinose-liberating enzyme or enzyme system, and the defined soluble monomeric or oligomeric building block is arabinose, wherein the enzyme or enzyme system used in the second enzymatic treatment of a) is a glucose-liberating enzyme or enzyme system, and the defined soluble monomeric or oligomeric building block is glucose, and wherein the enzyme or enzyme system used in the third enzymatic treatment of a) is a uronic acid-liberating enzyme or enzyme system, and the defined soluble monomeric or oligomeric building block is uronic acid.

18. The method of claim 1, wherein the enzyme or enzyme system used in the first treatment of a) is selected from the group consisting of Endoarabinase from *A. niger* and Arabinofucosidase from *A. niger*, wherein the enzyme or enzyme system used in the second treatment of a) is selected from the group consisting of Beta-glucosidase from *A. niger* or *T. reesei*, Cellobiohydrolase I-II from *T. reesei*, and Endo-beta-1-4-D -glucanase I-V from *T. reesei*, and wherein the enzyme or enzyme system used in the third treatment of a) is a Pectinase from *A. aculeatus, A. niger* or *C. japonicus*.

19. The method of claim 1, wherein the feedstock is a galactan-pectin-rich feedstock and wherein the enzyme or enzyme system used in the first enzymatic treatment of a) is a galactose-liberating enzyme or enzyme system, and the defined soluble monomeric or oligomeric building block is galactose, and wherein the enzyme or enzyme system used in the second enzymatic treatment of a) is a uronic acid-liberating enzyme or enzyme system, and the defined soluble monomeric or oligomeric building block is uronic acid.

20. The method of claim 1, wherein the enzyme or enzyme system used in the first treatment of a) is selected from the group consisting of Endogalactonase from *A. niger* or *C. thermocellum*, and beta-Galactosidase from *A. niger* or *K. fragilis*, and wherein the enzyme or enzyme system used in the second treatment of a) is a Pectinase from *A. aculeates, A. niger* or *C. japonicus*.

21. The method of claim 1, wherein the feedstock is a mannan-xylan-rich feedstock and wherein the enzyme or enzyme system used in the first enzymatic treatment of a) is a mannose-liberating enzyme or enzyme system, and the defined soluble monomeric or oligomeric building block is mannose, and wherein the enzyme or enzyme system used in the second enzymatic treatment of a) is a xylose-liberating enzyme or enzyme system, and the defined soluble monomeric or oligomeric building block is xylose.

22. The method of claim 1, wherein the enzyme or enzyme system used in the first treatment of a) is selected from the group consisting of Endo-Mannanase from *A. niger, B. subtilis, T. maritima* or *T. reesei*, and Exo-Mannosidase from *C. fimi*, and wherein the enzyme or enzyme system used in the second treatment of a) is selected from the group consisting of Endoxylanase from *A. niger* or *T. reesei* or *C. thermocellum*, and Xylosidase from *A. niger* or *T. reesei*.

23. The method of claim 1, wherein the feedstock is a mannan-cellulose-rich feedstock and wherein the enzyme or enzyme system used in the first enzymatic treatment of a) is a mannose-liberating enzyme or enzyme system, and the defined soluble monomeric or oligomeric building block is mannose, and wherein the enzyme or enzyme system used in the second enzymatic treatment of a) is a glucose-liberating enzyme or enzyme system, and the defined soluble monomeric or oligomeric building block is glucose.

24. The method of claim 1, wherein the enzyme or enzyme system used in the first treatment of a) is selected from the group consisting of Endo-Mannanase from *A. niger, B. subtilis, T. maritima* or *T. reesei*, and Exo-Mannosidase from *C. fimi*, and wherein the enzyme or enzyme system used in the second treatment of a) is selected from the group consisting of Beta-glucosidase from *A. niger* or *T. reesei*, Cellobiohydrolase I-II from *T. reesei*, and Endo-beta-1-4-D-glucanase I-V from *T. reesei*.

25. The method of claim 1, wherein the raw polymeric feedstock comprises cellulose and hemicellulose and the enzyme system used in a particular enzymatic treatment has cellulase activity, and optionally beta-glycosidase, glucohydrolase or alpha- or beta-amylase activity, but is essentially free of hemicellulase activity.

26. The method of claim 1, wherein the enzyme system used in a particular enzymatic treatment contains as contaminating enzymatic activities one or more of such enzymatic activities which have been employed in a previous enzymatic treatment using a different enzyme system or which can only cause liberation of other monomeric or oligomeric building blocks from polymeric feedstock that are initially essentially absent in the raw polymeric feedstock.

27. The method of claim 1, wherein the enzyme system used in a particular enzymatic treatment has a first enzymatic activity and contains at least one additional enzymatic activity, which leads to the same defined monomeric or oligomeric building block from the raw or processed polymeric feedstock as the first enzymatic activity of the enzyme system.

28. The method of claim 1, wherein the insoluble raw or processed polymeric feedstock is subjected to a selective or unselective physico-chemical treatment prior to a) or prior to repetition of a).

29. The method according to claim 28, wherein the physico-chemical treatment comprises a treatment with aqueous solvents, organic solvents, or any combination or mixtures of these with ethanol or glycerol.

30. The method according to any one of claims 16, 18, and 20, wherein the Pectinase is pectate lyase.

31. The method according to any one of claims 16, 18, and 20, wherein the Pectinase is polygalactourenase.

32. The method of claim 1, wherein the enzyme system used in a) comprises not more than 10% of contaminating enzyme activities apart from an enzyme activity resulting in liberation of said defined soluble monomeric or oligomeric building blocks from the insoluble raw polymeric feedstock according to a).

33. The method of claim 1, wherein the enzyme system used in a) comprises not more than 2% of contaminating enzyme activities apart from an enzyme activity resulting in liberation of said defined soluble monomeric or oligomeric building blocks from the insoluble raw polymeric feedstock according to a).

34. The method of claim 1, wherein the enzyme system used in a) comprises not more than 1% of contaminating enzyme activities apart from an enzyme activity resulting in liberation of said defined soluble monomeric or oligomeric building blocks from the insoluble raw polymeric feedstock according to a).

35. The method according to claim 1, wherein the enzyme system used in a) comprises an enzyme activity resulting in the liberation of said defined soluble monomeric or oligomeric building blocks from the insoluble raw polymeric feedstock according to a), wherein said enzyme activity is at least 99% of all enzyme activities present in the enzyme system.

36. The method according to claim 1, wherein the enzyme system used in a) comprises an enzyme activity resulting in the liberation of said defined soluble monomeric or oligomeric building blocks from the insoluble raw polymeric feedstock according to a), wherein said enzyme activity is at least 95% of all enzyme activities present in the enzyme system.

37. The method according to claim 1, wherein the enzyme system used in a) comprises an enzyme activity resulting in the liberation of said defined soluble monomeric or oligomeric building blocks from the insoluble raw polymeric feedstock according to a), wherein said enzyme activity is at least 90% of all enzyme activities present in the enzyme system.

38. The method according to claim 1, wherein the enzyme system used in a) comprises an enzyme activity resulting in the liberation of said defined soluble monomeric or oligomeric building blocks from the insoluble raw polymeric feedstock according to a), wherein said enzyme activity is at least 80% of all enzyme activities present in the enzyme system.

* * * * *